United States Patent
Shevitz

(10) Patent No.: US 11,773,361 B2
(45) Date of Patent: Oct. 3, 2023

(54) BIOREACTORS

(71) Applicant: Jerry Shevitz, Livingston, NJ (US)

(72) Inventor: Jerry Shevitz, Livingston, NJ (US)

( * ) Notice: Subject to any disclaimer, the term of this patent is extended or adjusted under 35 U.S.C. 154(b) by 565 days.

(21) Appl. No.: 16/612,460

(22) PCT Filed: May 10, 2018

(86) PCT No.: PCT/US2018/032140
§ 371 (c)(1),
(2) Date: Nov. 11, 2019

(87) PCT Pub. No.: WO2018/209133
PCT Pub. Date: Nov. 15, 2018

(65) Prior Publication Data
US 2020/0165558 A1    May 28, 2020

Related U.S. Application Data

(60) Provisional application No. 62/505,250, filed on May 12, 2017.

(51) Int. Cl.
*C12M 1/04* (2006.01)
*C12M 1/00* (2006.01)
*B01F 23/233* (2022.01)
*B01F 27/91* (2022.01)
*B01F 35/10* (2022.01)
*B01F 35/50* (2022.01)

(52) U.S. Cl.
CPC ............ *C12M 27/04* (2013.01); *B01F 23/233* (2022.01); *B01F 27/91* (2022.01); *B01F 35/146* (2022.01); *B01F 35/514* (2022.01); *C12M 23/28* (2013.01); *C12M 23/38* (2013.01); *C12M 29/06* (2013.01)

(58) Field of Classification Search
CPC ...... C12M 27/04; C12M 23/28; C12M 23/38; C12M 29/06; B01F 35/514; B01F 23/233; B01F 35/146; B01F 27/91
See application file for complete search history.

(56) References Cited

U.S. PATENT DOCUMENTS 3,867,488 A * 2/1975 Porterfield .............. C02F 3/205
                                                        261/87
4,019,962 A * 4/1977 Allen ..................... C12M 27/20
                                                        435/921

(Continued)

OTHER PUBLICATIONS

Pall Life Sciences. Introducing iCELLis Nano bioreactor. Posted on internet Mar. 15, 2018.

(Continued)

*Primary Examiner* — William H. Beisner
*Assistant Examiner* — Danielle B Henkel
(74) *Attorney, Agent, or Firm* — Law Firm of Allan Fried; Allan H. Fried

(57) ABSTRACT

Miniature stirred tank bioreactor and system; the bioreactor configured for single use culturing providing unobstructed culturing volume with sensors, probes and ports using minimally invasive placement in-wall or across the wall methods; the bioreactor further capable of containing scaffolds and features for culturing cells and tissue, including structures providing surfaces for cell growth, and screens for retaining microparticles during media exchange.

19 Claims, 38 Drawing Sheets

(56) References Cited

U.S. PATENT DOCUMENTS

| | | | | | |
|---|---|---|---|---|---|
| 4,231,974 | A * | 11/1980 | Engelbrecht | ............ | C02F 3/207 261/87 |
| 4,888,294 | A * | 12/1989 | Van Wezel | ............ | C12M 33/10 435/295.3 |
| 10,260,036 | B2 * | 4/2019 | Shor | ...................... | C12M 33/14 |
| 2005/0239199 | A1 * | 10/2005 | Kunas | .................... | C12M 23/06 435/297.1 |
| 2009/0280565 | A1 * | 11/2009 | Jolicoeur | ............... | C12M 29/04 435/303.1 |
| 2010/0178685 | A1 * | 7/2010 | Kloss | .................. | B01F 23/2331 435/243 |
| 2011/0013474 | A1 * | 1/2011 | Ludwig | .................. | C12M 29/06 366/140 |
| 2011/0033918 | A1 * | 2/2011 | Asnaghi | ................. | C12M 25/14 435/289.1 |
| 2011/0053486 | A1 * | 3/2011 | Holtz | .................... | C12M 37/00 29/428 |
| 2012/0275260 | A1 * | 11/2012 | Haas | ...................... | B01F 27/862 366/314 |
| 2015/0003189 | A1 * | 1/2015 | Werth | ................. | B01F 33/4534 366/273 |
| 2015/0218501 | A1 * | 8/2015 | Kauling | ................. | C12M 29/20 435/325 |
| 2015/0368602 | A1 * | 12/2015 | Galliher | ................. | C12M 27/02 435/293.1 |
| 2017/0362555 | A1 * | 12/2017 | Damren | ................. | C12M 27/04 |

OTHER PUBLICATIONS

Pall Life Sciences. Introducing iCELLis Nano bioreactor. Posted on internet Mar. 15, 2018. Internet link: https://www.pall.com/en/biotech/news/2018-03-15.html.

ReseaChem. ATMI iCELLis™ Nano system. 2016.

Pall Life Sciences. Bringing Fast Process Development to Adherent Cell Culture Process: Demonstration of Linear Scalability from 1.6 to 200 m2 in Single-Use Fixed Bed Reactor. 2015.

Sartorius Sartorius Stedim Biotech Introduces Mini Microcarrier Bioreactor for Culturing Adherent Cells. Posted on Internet Apr. 20, 2018 Internet link: https://www.sartorius.com/en/company/newsroom/product-news/16116-16116.

Sartorius Sartorius Stedim Biotech Introduces Mini Microcarrier Bioreactor for Culturing Adherent Cells. Posted on Internet Apr. 20, 2018.

Sartorius Sartorius.com/download/24008/20180420-ssb-e-ambr-250ht-microcarrier-data.pdf. Picture of Sartorius Bioreactor. Posted on Internet Apr. 20, 2018.

Applikon Biotechnology https://www.youtube.com/watch?v=AxJpXwKiBsw. Picture of Applikon MinBio V2 bioreactor in process of being added to its stand, taken at 0:48 of this YouTube video which video was posted on the internet Apr. 20, 2017.

Applikon Biotechnology https://www.youtube.com/watch?v=AxJpXwKiBsw. Picture of Applikon MinBio V2 bioreactor taken at 0:58 of this YouTube video which video was posted on the internet Apr. 20, 2017.

Eppendorf https://www.youtube.com/watch?v=m12V8CwB7p8. Picture of Eppendorf bioreactor with control station taken at 0:24 of this YouTube video which video was posted on the internet on May 2, 2017.

Zurich University https://www.youtube.com/watch?v=y0F3jHjVyb4. Picture of the Uni Vessel SU Sartorius bioreactor taken at 0:43 of this video which video was posted on the internet on Oct. 26, 2016.

Sartorius https://www.youtube.com/watch?v=COqVUbd41No. Picture of Sartorius Biostat Benchtop Bioreactor taken at 2:50 of this video which video was posted on the internet in 2014.

* cited by examiner

BIOREACTORS

CROSS REFERENCE TO RELATED APPLICATIONS

This application is a National Phase application of PCT international Application No. PCT/US2018/032140, international filing date May 10, 2018. This application and said PCT International Application both claim the benefit of U.S. provisional application No. 62/505,250 filed May 12, 2017. The entire disclosures of the foregoing PCT International Application and provisional application are each incorporated herein by reference in its entirety.

FIELD OF THE INVENTION

The field of the invention is bioreactors, in large part, small portable disposable bioreactors.

BACKGROUND OF THE INVENTION

The culture of cells in vitro is an ever evolving process. Specifically, as it relates to advancements in cell biology of animal and mammalian cells, new cells are being discovered or developed at a rapid rate. Those include stem cells, recombinant cells, and cells based on selection processes and genetic alteration; all contribute to the growing pool and variations of cell lines. With those advancements, methods for culturing cells are also evolving. Fundamentally, however, essentially all culture systems are similar and the culture requirement of these cells are basically also similar.

Regardless how cells are cultured, they have basic needs in order to sustain their metabolism, viability and their ability to propagate. Those requirements may be loosely divided into two categories; one, control of the physical environment of the cell, including temperature, means of maintaining the cells in space preferably in a uniform manner to maintain culture homogeneity, control of flow dynamics within or across the culture, addition and removal of gases, etc.; two control of the metabolic or chemical environment of the cell, including maintaining the nutrients required for cell growth, regulatory constituents that promote or regulate cell activity and the ability to address harmful waste generated by the cell, etc. A system for culturing cells must provide for those or similar requirements. The stirred tank is generally considered as the most effective for maintaining the homogeneity of the culture. Such culture systems are commonly referred to bioreactors or fermenters.

Most bioreactor systems are based on technology that is proven and decades old; however, as cell biology technology evolves so have some of the culturing requirements; for example, cost of medium and supplements have increased substantially, particularly the cost of highly specialized reagents. The use of large bioreactors has become impractical with such costly reagents. Maintaining a continuous culture, requiring continuous maintenance, is also very costly in a large vessel. Therefore, for many applications, smaller systems are more desirable.

One may consider a "large" system as one having a foot-print>one foot squared and more commonly>two ft. squared. (For purposes of this application, the foot print is the cross sectional area at the base of the system.) The "large" system also contains a relatively large culture vessel or bags, i.e., >0.5 L, more commonly>1.0 L. It is desirable therefore to confine the features of the stirred tank in a small volume bioreactor. Additionally, the typical bioreactor is of sufficient size and design to accommodate devices that monitor and control the condition of the culture. These may includes sensing probes such as for pH, dissolved oxygen (DO), temperature, etc. These sensors or probes are typically inserted into the culture medium. While such placement provides a direct reading of the culture, they also interfere with uniform mixing of the culture and they serve as surfaces to which cells may attach in large numbers. Many primary cell lines or stem cells, which are highly adherent, will readily attach to such surfaces. In small bioreactors, <0.5 L such inserts can cause significant inhomogeneity in the culture, greatly effecting the results of the culture; in addition, inserts inside the culture, particularly in a small vessel can limit the use of other platforms or accessories that may be used to grow or regulate the growth of specific cells, as will be described further on. In "bag" based bioreactor systems, while the problem of inserts has been largely solved by using noninvasive optical sensors, predominantly for pH and dissolved oxygen, mixing is more of a challenge. It is more difficult and costly to incorporate an impeller into the bag bioreactor and to couple it to motor drive, That becomes increasingly difficult the smaller the bag, particularly bags with working volume of <10.0 L. Typically, mixing is achieved by shaking or rocking the bag. The very nature of a bag bioreactor is a flat layout, which entails a horizontal layout of the supporting platform and control system; therefore, even for a small bag bioreactor system, the foot print can be significant, taking up valuable bench work space. Miniaturization of stirred tank bioreactor has been achieved with various degrees of success; however in such systems, the bioreactors are coupled or integrated with a large control system, so the overall foot print remains large; furthermore, such small systems may not contain the complete complement of controls required for precise control of a sensitive culture.

The current invention is uniquely designed to address some of the "problems" encountered by practitioners of cell culture, when dealing with the various requirements of the many different cell lines and their peculiarities. The stirred tank bioreactor of the current invention is a disposable devise that is supplied sterile to the user with all the essential accessories ready for immediate use. Typically the material of construction is polycarbonate or similar material compatible with cell growth and viability. It is well known that that bench table top work space is highly limited and highly desirable, particularly in many cramped laboratory facilities. The current invention addresses this problem by providing a "complete" bioreactor system in a very small foot print for example, 4.25 inches or 4 inches wide by 8.5 inches deep (or 8 inches deep), and with a height that normally varies between 10" and 13". One can place 3 complete systems next to each other, openly, in about one foot square of bench top space. That can be multiplied by stacking the systems. Along with the small foot print, the bioreactor or culture vessel of the system is also small, typically, 35 to 100 ml working volume, although smaller or larger culture systems may be used. In spite of the small size, the system of the current invention incorporates features that provide the user with the culture control flexibility and capabilities of a larger system. An added benefit of the small size is a substantial savings in the cost of operating the system; substantially less medium is required to operate the smaller system, substantially less of rare and costly additives are needed. These features become quite significant in a continuous culture, which is maintained for extended durations. An additional feature of the current invention, other than the agitation system, is the elimination of all inserts into the culture vessel, one gains working volume and less interference. As previously indicated such inserts can interfere with the culture, particularly in a small culture vessel. Other features of the current invention, designed to enhance the process of cell culture will become apparent and will be described in greater detail.

BRIEF DESCRIPTION OF THE DRAWINGS

FIG. 6B Top view of a bioreactor system of the invention (where both a manifold (30) on the left side of the system and a pump (31) on the left side of the system have been displaced from the system to make them visible (most visible electrical, gas and liquid lines have been omitted from the Figure.)

BRIEF SUMMARY OF THE INVENTION

Figure 1A:
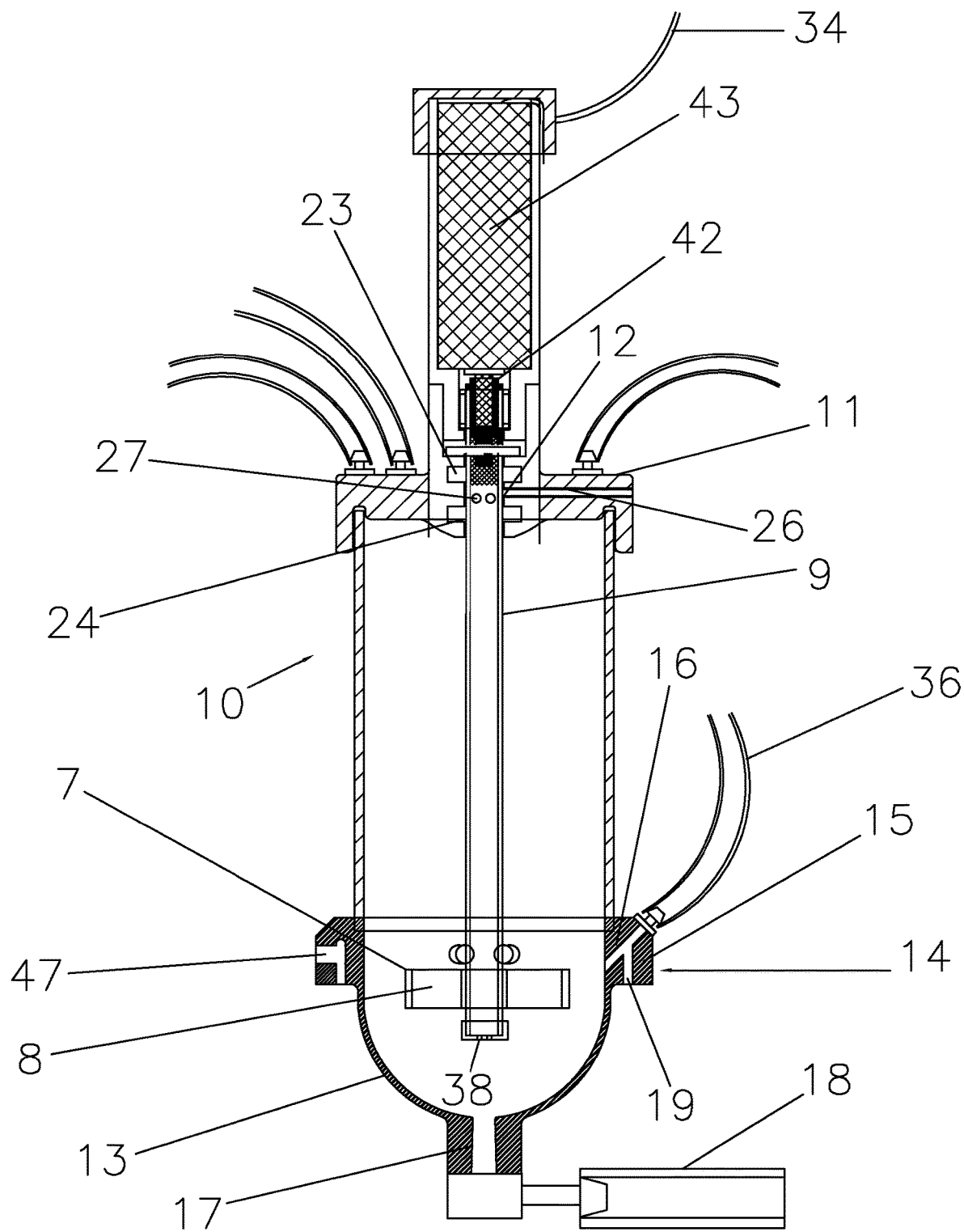
FIG. 1A Partial cross-sectional view of a bioreactor vessel of the invention.
Figure 1B:
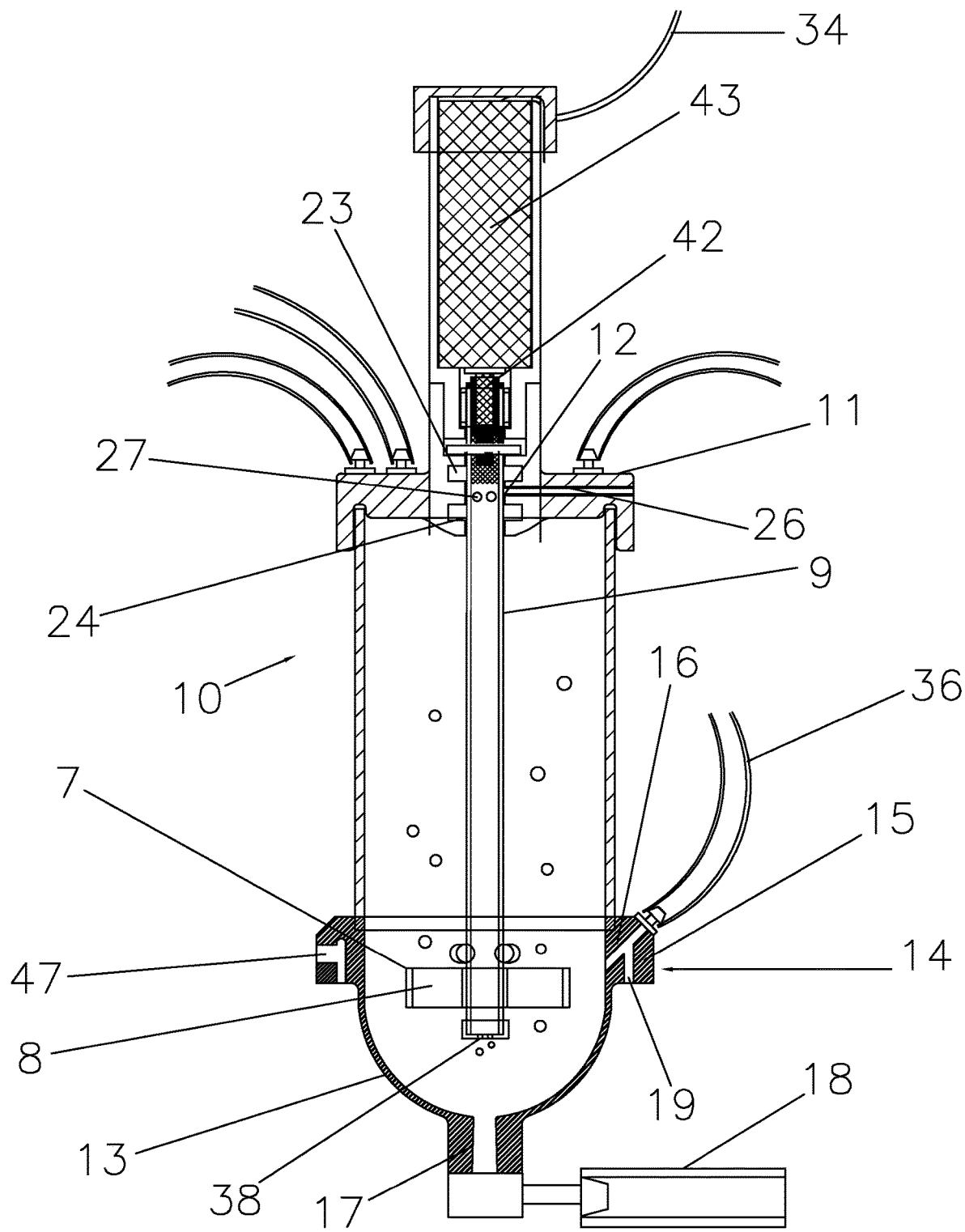
FIG. 1B View of FIG. 1A showing bubbles in liquid in the bioreactor vessel.
Figure 2A:
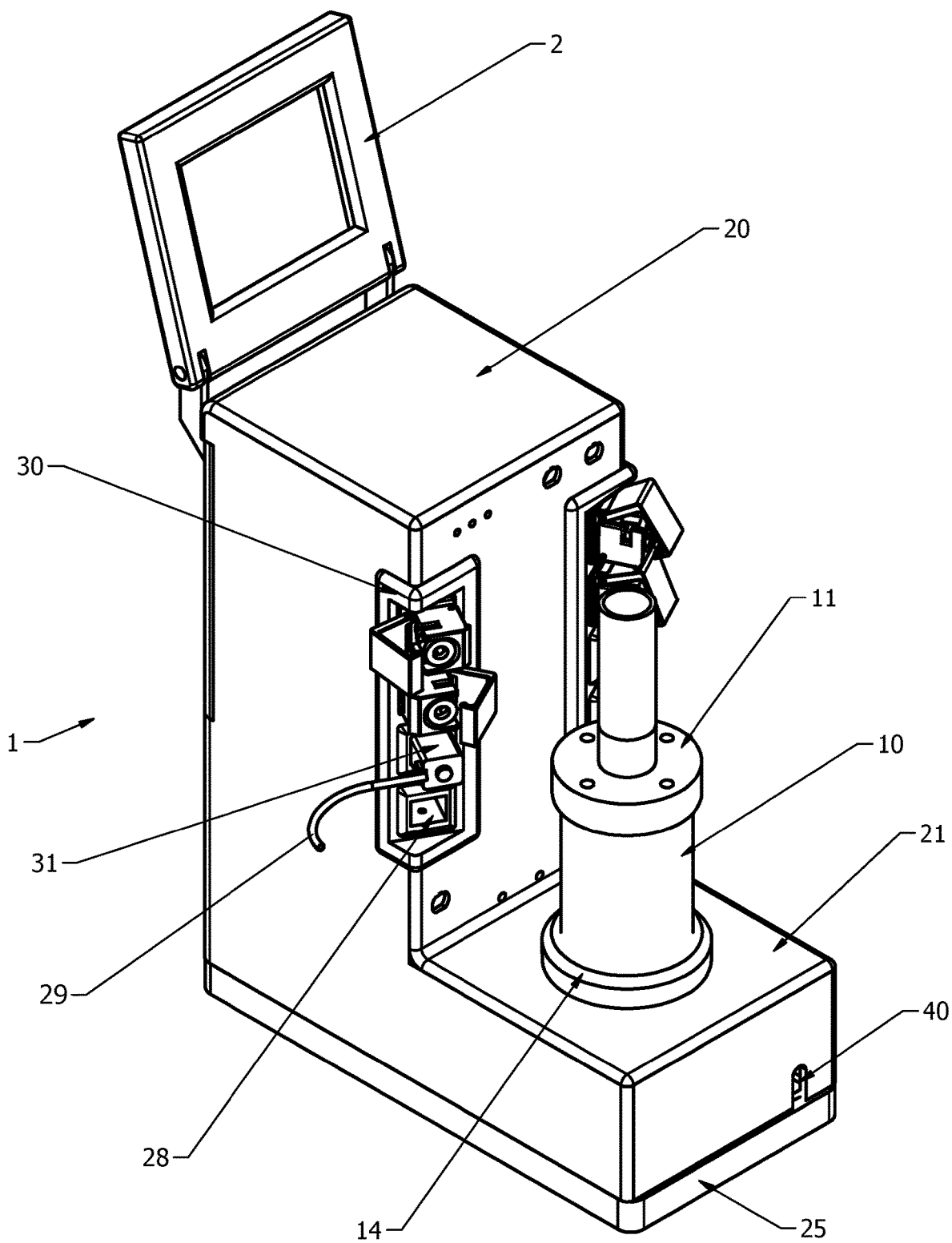
FIG. 2A-2E Perspective views of bioreactor systems of the invention (the motor for the impeller shaft and most electrical, gas and liquid lines have been omitted from the Figures.)
Figure 2B:
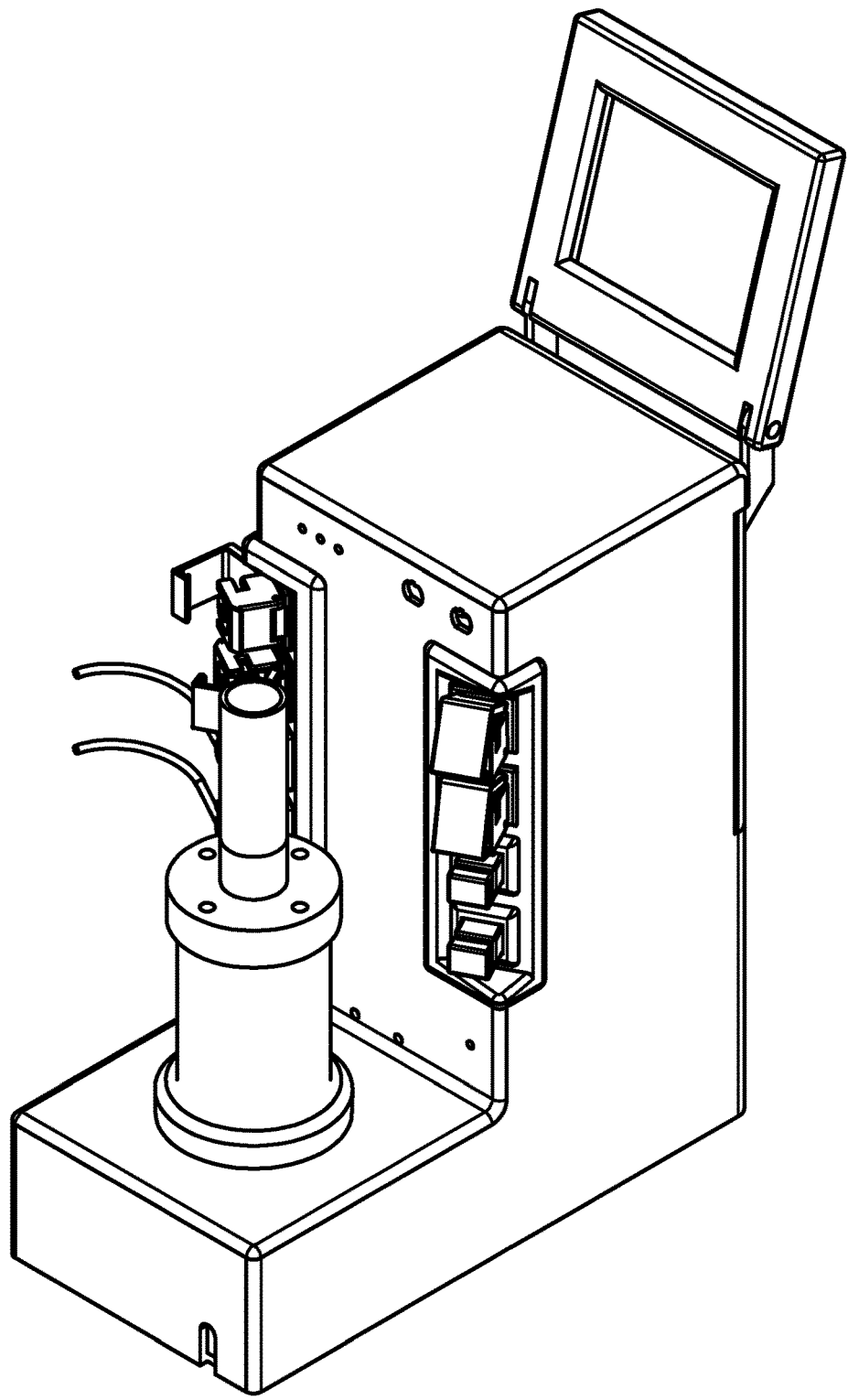
Figure 2C:
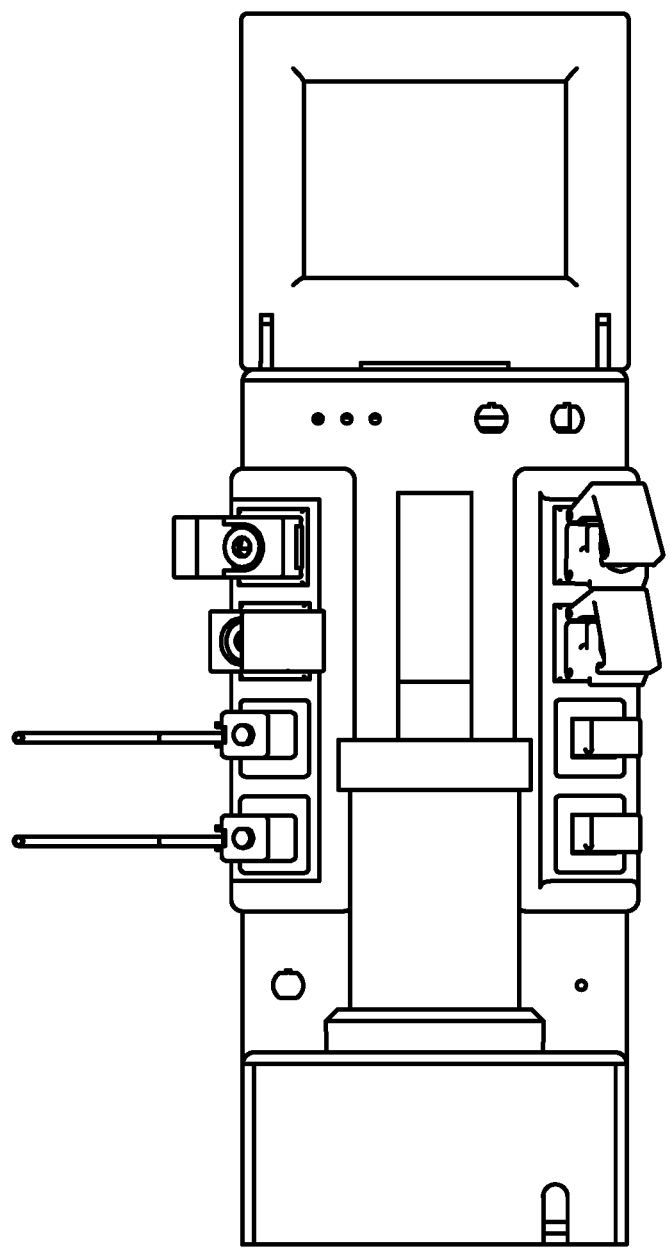
Figure 2D:
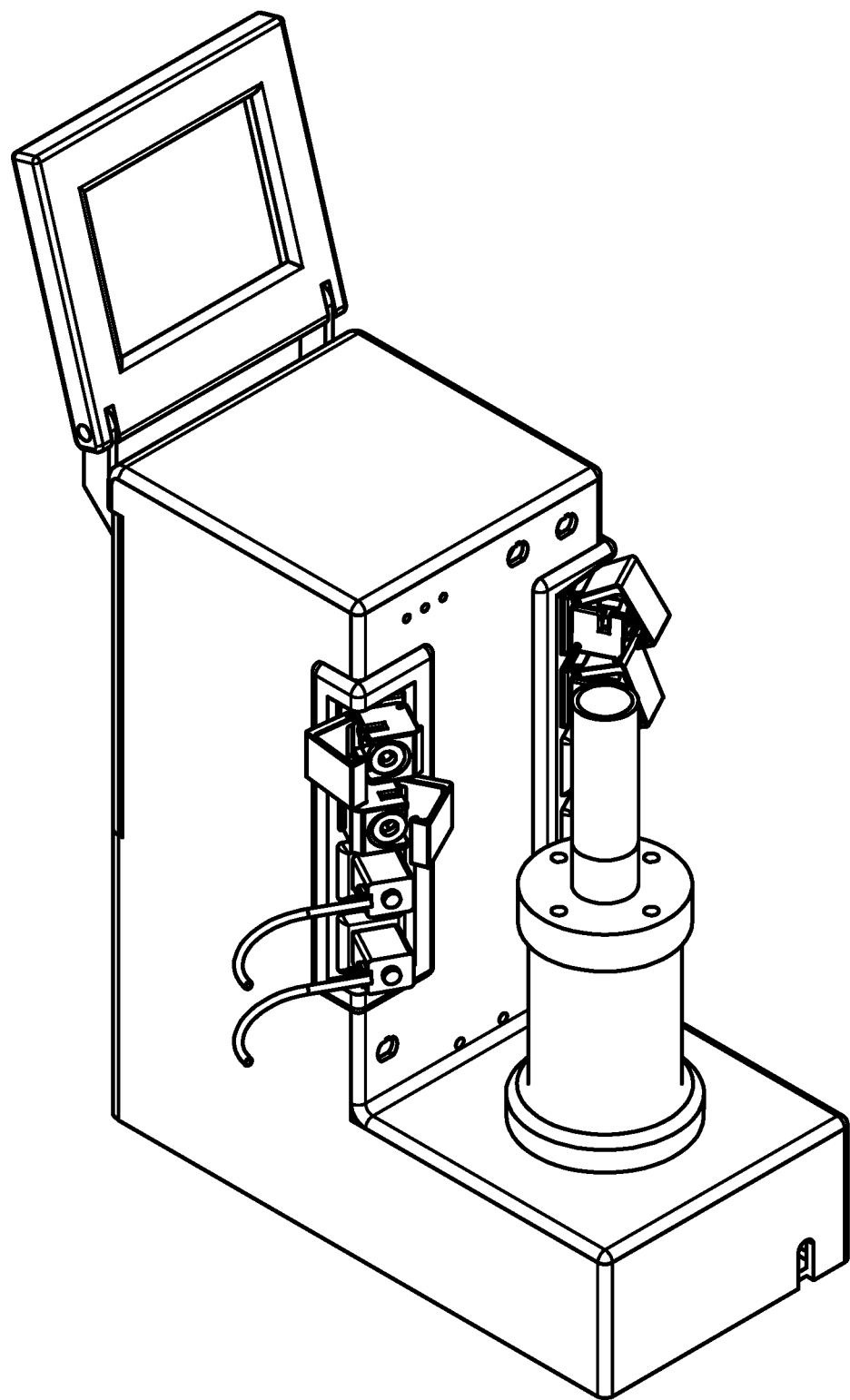
Figure 2E:
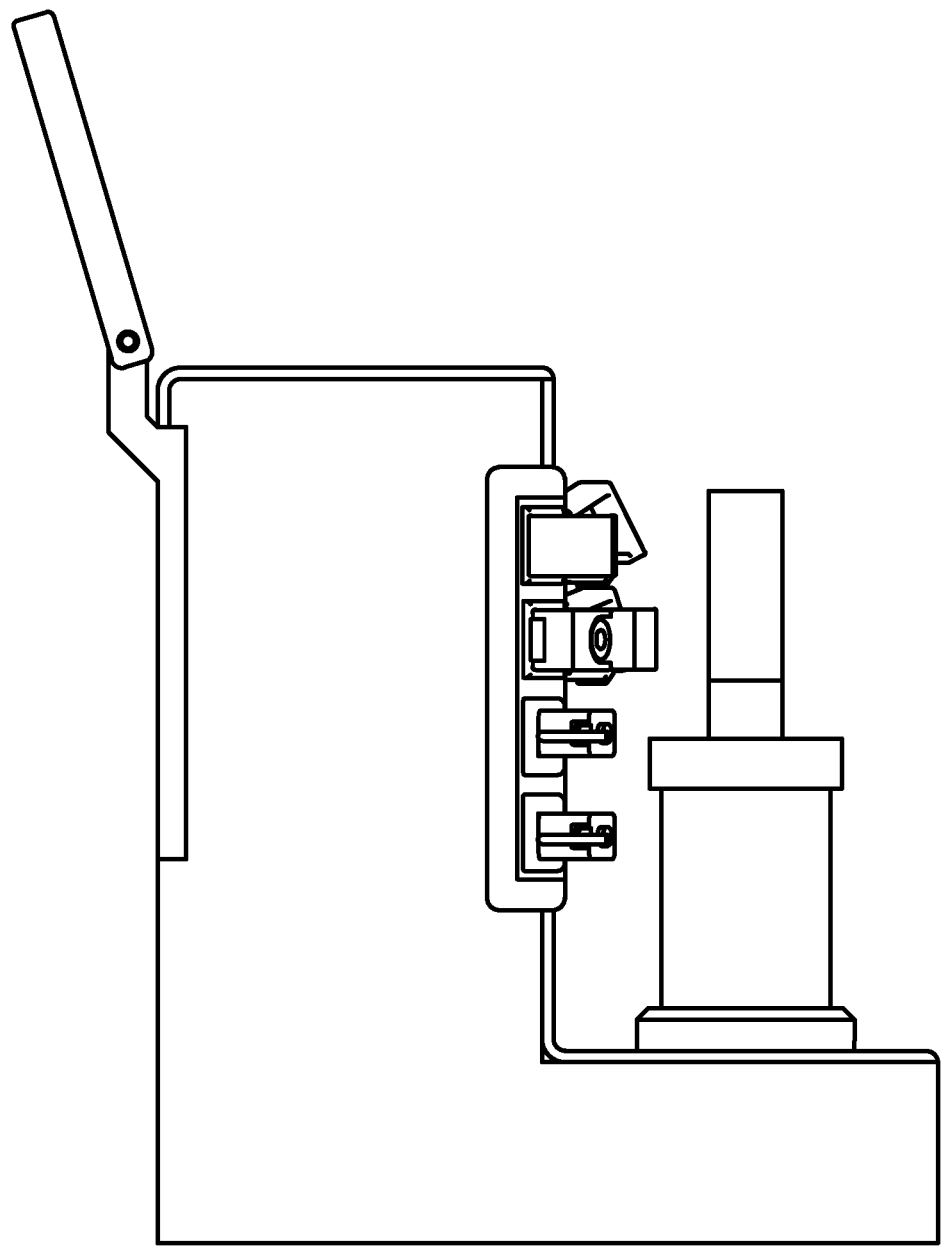
Figure 3A:
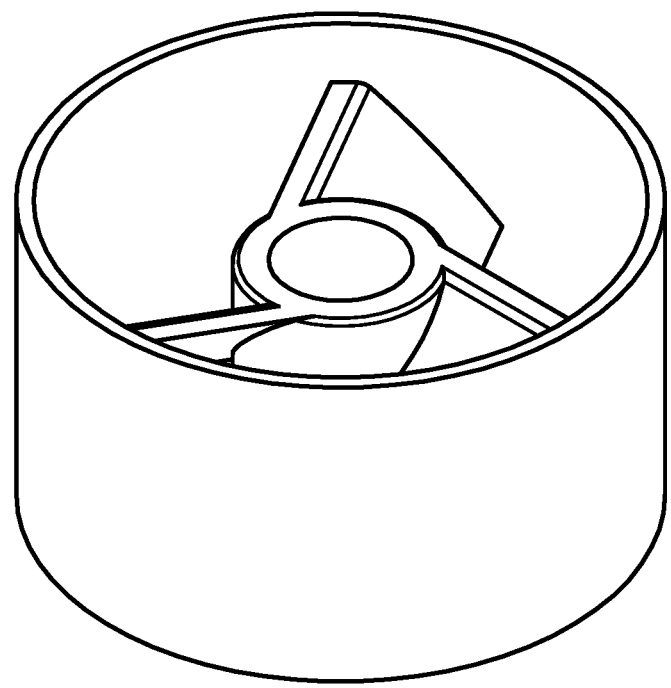
FIG. 3A Perspective view of an impeller of the invention surrounded by a draft tube of greater height.
Figure 3B:
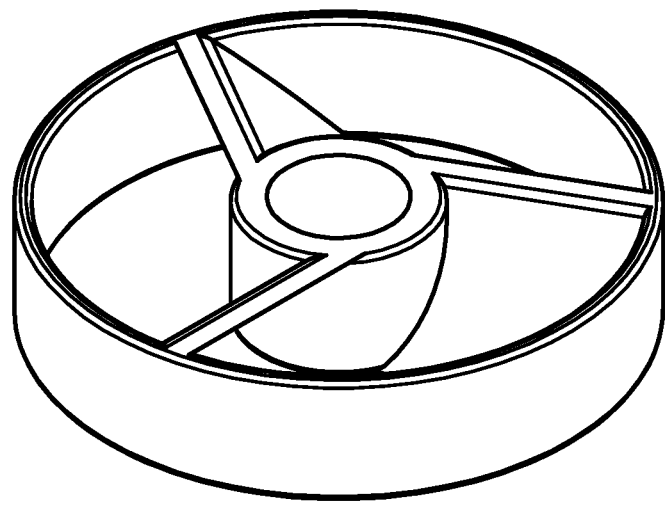
FIG. 3B-3D Perspective, top and side views, respectively, of an impeller of the invention surrounded by a draft tube of equal height.
Figure 3C:
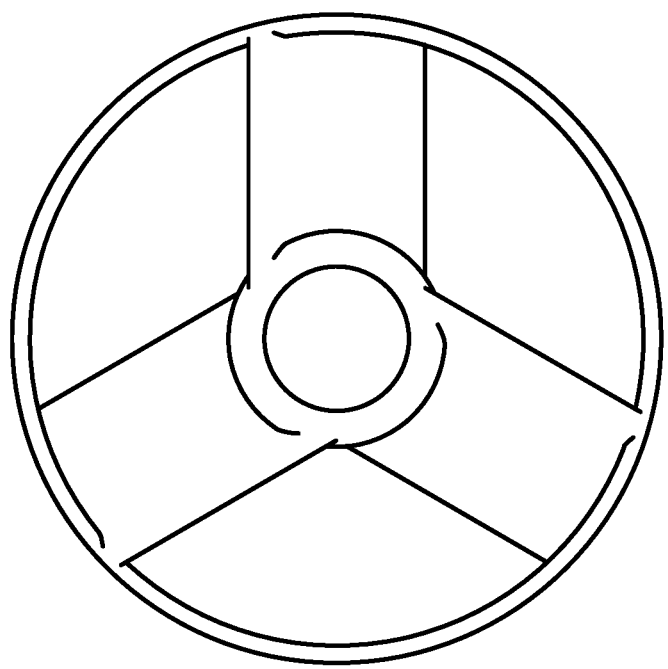
Figure 3D:
Figure 4A:
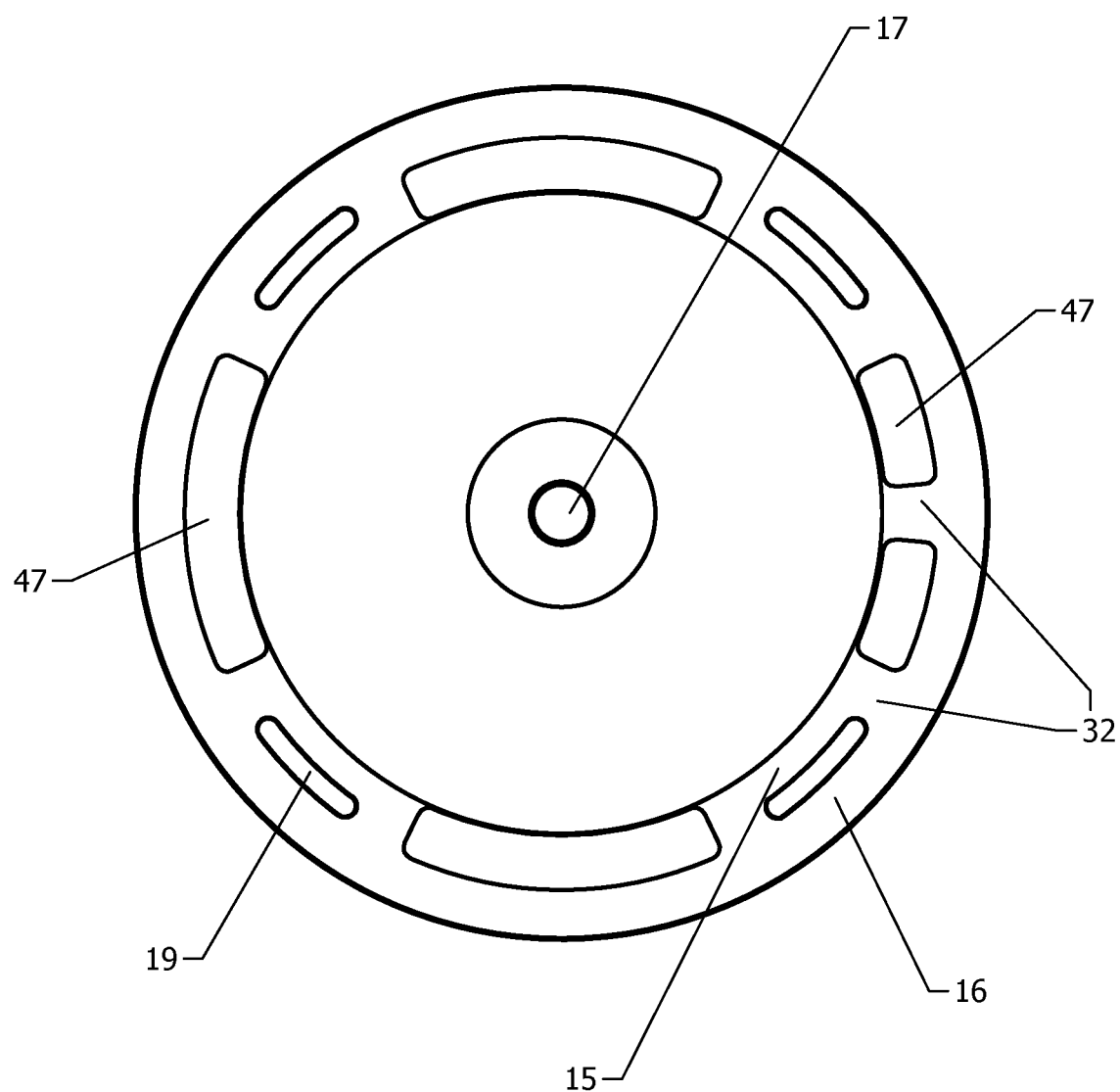
FIG. 4A-4C The lower portion (approximately one-third) of a bioreactor vessel of the invention shown from a bottom view, cross-sectional view, and top view, respectively.
Figure 4B:
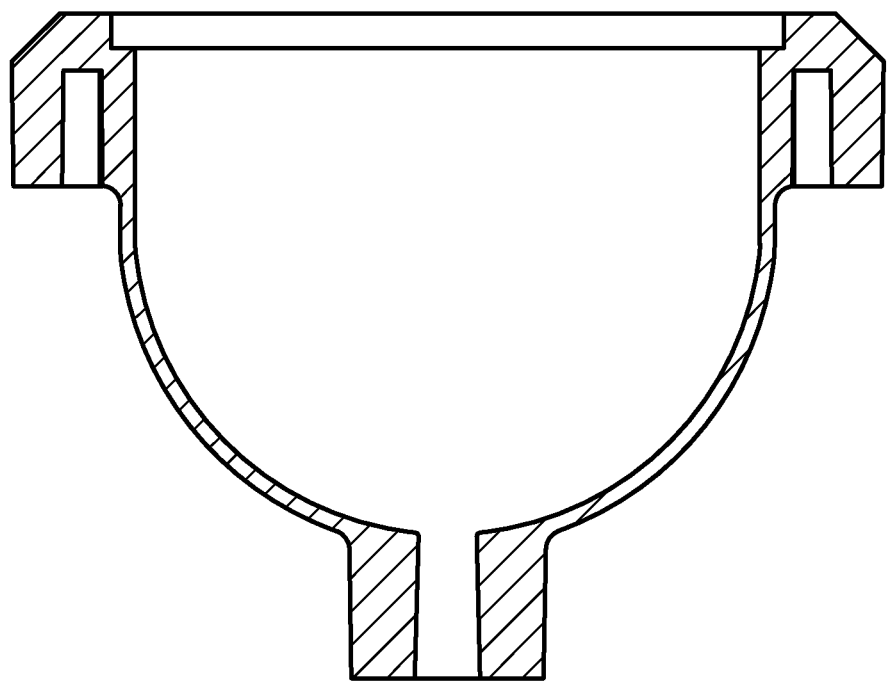
Figure 4C:
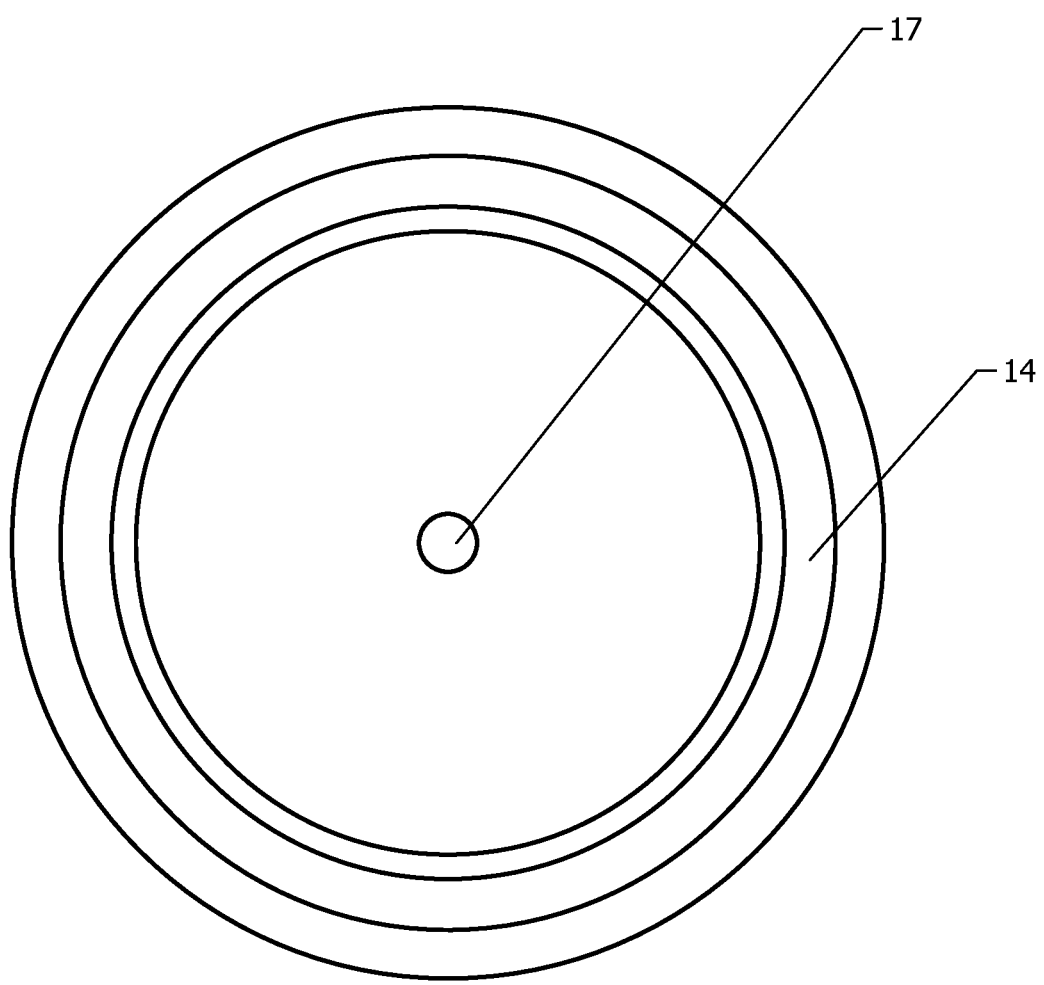

As described herein is a small portable single use stirred tank bioreactor vessel, small systems designed to employ it, and interconnected arrays of two or more those systems.

Also described are bioreactors with scaffolding for cell growth, bioreactors with stirrer shafts comprising spaced concentric tubes that provide surfaces for cell growth, bioreactors with vertical columns which provide surfaces for cell growth, and bioreactors with a screened enclosure for retaining microcarriers while exchanging media.

DETAILED DESCRIPTION

In one aspect, the invention is a disposable stir tank bioreactor vessel, said vessel having a working volume of about 100 ml or less said vessel comprising a head plate, said head plate comprising an opening through which a gas such as air can be delivered into the interior of the vessel and a drainage tube through which fluid can exit the vessel, said vessel surrounded by a rim to which sensor devices can be added, said vessel further comprising an impeller (stirrer) shaft, said shaft vertically disposed, said vessel being sterile.

In certain embodiments, the disposable stir tank bioreactor comprises one or more patch sensors (thin and flat, preferably with a thickness of less than 1 mm) attached to the inner surface of the vessel. Some examples of the patch sensor are ones selected from the group consisting of a pH sensor, a temperature sensor, carbon dioxide sensor or a dissolved oxygen (DO) sensor.

In certain embodiments, the disposable stir tank bioreactor vessel is covered by a removable head plate, which head plate allows full access to the vessel. The head plate preferably comprises an opening for an impeller shaft. The head plate preferably contains two sealing rings surrounding the impeller shaft, wherein the rings are separated so that an opening in the shaft between the two rings can connect to a gas source. The drive shaft preferably extends from above the head plate and, via an opening in the head plate, into the vessel.

The disposable stir tank bioreactor vessel is preferably made of plastic (most preferably polycarbonate) and is preferably transparent.

In some preferred embodiments, the rim of the disposable stir tank bioreactor vessel is a "double rim" (one with an outwardly hanging lip) to which sensor devices can be added in the rim space, the rim space being the space under and inside the lip. Said rim space may comprise rim compartments separated by ribs (or walls).

A system aspect of the invention a system, specifically a disposable stir tank bioreactor system, said system comprising a bioreactor controller and a vessel of any of the foregoing claims, said system with a footprint not exceeding 100 square inches (preferably not exceeding 32 square inches) and a height not exceeding 20 inches (preferably not exceeding 13 inches).

In preferred embodiments, the disposable stir tank bioreactor system comprises a bioreactor controller plus any of the disposable stir tank bioreactor vessels of the invention, or its various embodiments, including its preferred embodiments. In some embodiments, the controller housing comprises a controller that controls at least one variable (e.g., pH, dissolved oxygen, or temperature). The housing will preferably comprise a vessel receptacle, preferably part of or attached to a heating block.

The bioreactor control will preferably comprise, a controller housing, one or two pump manifolds, each manifold comprising a plurality (one or more) of pump banks (a/k/a receptacles) upon which a peristaltic pump is placed, each pump comprising a motor with a rotatable shaft, a pump base and a pump head, said base comprising a surface with a groove, said head comprising rollers, said groove and rollers for engaging tubing and driving fluid through the tube by a peristaltic displacement mechanism, wherein each pump manifold is vertically disposed along on a corner of the controller housing, said corner along the edge of a front surface of the controller housing, such that said front surface faces a bioreactor vessel placed on the vessel receptacle, wherein the motor shaft axis is at angle greater than zero (preferably in the range 20 to 45 degrees, more preferably about 30 degrees) away from said front surface so that it will not point at a bioreactor vessel on the vessel receptacle.

Preferably, in at least one rim compartment there is a sensory device, especially one that comprises a patch sensor inside the vessel.

In particular aspects, the disposable stir tank bioreactor vessel of the invention comprises a vertically disposed drive shaft (a/k/a "impeller shaft") said drive shaft extending from above the head plate and, via an opening in the head plate, into the vessel.

In particular embodiments of the disposable stir tank bioreactor, the drive shaft comprises a hollow vertical core so that a gas, such as oxygen, can enter at the top of said vertical core, and the drive shaft comprises an opening at one or more places along its length, so that the gas can exit the hollow core and enter the interior of the vessel, including entering fluid inside the vessel. In other particular embodiments, the drive shaft comprises one or more impellers anywhere along the shaft, preferably at its lower end. In particular embodiments, the impeller is connected to and surrounded by a draft tube attached to the impeller at its periphery. (Accordingly the draft tube rotates in the same direction as the impeller. The draft tube may be the same height as the impeller blade or extend above it or below it).

In some aspects of the disposable stir tank bioreactor system, the drive shaft comprises holes and accordingly is a sparger that discharges bubbles, the holes/sparger is preferably at the base of the drive shaft.

In preferred aspects, the disposable stir tank bioreactor system further comprises a battery or battery pack that is connected to and provides electrical power to the entire system in a manner that the entire system may be relocated while fully operational (preferably to a biological safety hood).

In preferred aspects, the disposable stir tank bioreactor system comprises both a display screen and a central processing unit that connects one or more sensor devices to the display screen and translates the information obtained by the sensor into an image (words, numbers, graphs, etc.) on the screen.

In an array aspect of the invention, there is a disposable stir tank bioreactor array, said array comprising a plurality (two or more) of bioreactor systems of any one of the above claims, in which each vessel is connected via its drainage tube directly to another bioreactor, said connection optionally including the drainage tube of the other bioreactor.

In a preferred embodiment of the array invention, one vessel is a controller bioreactor vessel (a/k/a master bioreactor) and any other vessel is an auxiliary bioreactor vessel, and in which at least one system variable (e.g., pH, dissolved oxygen, or temperature) is directly controlled, in full or in part, only in the controller bioreactor and wherein mixing and exchange of fluid between the controller bioreactor and the other occurs.

In a method aspect of the invention, the method comprises using any one of the above vessels, systems or arrays in a process for growing biological cells (human cells, animal cells, or microorganisms)

In a manifold aspect of the invention, the manifold comprising pump banks, which banks which can interchangeably receive different pumps, valves, and/or switches.

Preferably, the disposable stir tank bioreactor vessel has a working volume in the range 35 ml to 100 ml. Preferably, the vessel is disposable. Preferably, the vessel is spherical in a cross-section in a horizontal plane.

Preferably, the head plate of the vessel comprises a conduit capable of directing a flow of gases from the periphery of the head plate to the impeller shaft vertically disposed in the head plate. Preferably there is a cavity in the head plate, such that said cavity is located between the impeller and said conduit, and wherein said cavity is airtight in that gas delivered under pressure to said cavity cannot escape said cavity when gas flow is blocked by the impeller shaft and in that ambient air cannot enter the cavity from outside the bioreactor. Preferably, opposing mechanical slip seals form the upper and lower surfaces of the cavity. Preferably the impeller drive shaft is made of glass or other material resistant to wear caused by the slip seals, yet may be sterilized by gamma radiation.

Preferably, compartments in the double rim of the vessel comprise a lower wall to form a closed compartment (a/k/a "chamber"). Preferably, the closed compartment has one or more properties selected from the group consisting of (1) being capable of containing fluid and (2) being capable of having a property of its contents being communicated to a bioreactor controller. The double rim, for example, may contain a reference pH electrode that is in contact with the fluid in the vessel via a conductive bridge so that the reference electrode, the fluid in the vessel, an ISFET sensing the pH of the fluid, and a controller board form a closed circuit.

Preferably a double rim of a vessel has one or more properties selected from the group consisting of the following: it provides a place for attaching sensors located in the air gap to the wall of the vessel, its inner wall provides a transparent window to the vessel, its outer rim wall may be used to anchor and position a sensor in the rim, a temperature sensor may be inserted into a well in the inner rim wall, there is insulation of the gap between the rims, leads from a probe to the outer rim wall are secured in the wall, (Additionally, for full penetrations through the rim and vessel inner wall, such as for insertion of ports and conduits across the rim into the vessel, the double wall provides a convenient means to secure and seal such inserts in the rim body.) Preferably the double rim comprises an opening or port allowing full penetration of adapters, conduits or sensors across and through the rim and vessel inner wall. Preferably, in the double rim the luer type fittings are used to secure probes, conduits or sensors.

In particular embodiments of the vessel, an ISFET pH sensor or other ISFET sensor is embedded in the bioreactor vessel wall, its sensor tip positioned to contact fluid in the vessel. In particular embodiments, the vessel comprises or is attached to a reference electrode.

In particular embodiments of the vessel, the rim comprises a male luer lock fitted with an oxygen sensing probe or other sensing probe and further comprises a female luer lock adapter. For example, the rim may comprise a leur lock with both a second male luer lock and a compression fitting containing a fiber optic cable that can be reversibly fitted into the fitting.

In particular embodiments of the system, the system comprises a manifold that is an array with multiple pump banks or receptacles for pumps.

In a bioreactor controller aspect of the invention, there is a bioreactor controller comprising a controller housing, a vessel receptacle upon which a bioreactor vessel can be placed, said vessel receptacle part of or attached to a heating block, and/or one or two pump manifolds, each manifold comprising a plurality (one or more) of pump banks (a/k/a receptacles) upon which a peristaltic pump is placed, each pump comprising a motor with a rotatable shaft, a pump base and a pump head, said base comprising a surface with a groove, said head comprising rollers, said groove and rollers for engaging tubing and driving fluid through the tube by a peristaltic displacement mechanism, wherein each pump manifold is vertically disposed along on a corner of the controller housing, said corner along the edge of a front surface of the controller housing such that said front surface faces a bioreactor vessel placed on the vessel receptacle, wherein the motor shaft axis is at angle greater than zero (preferably in the range 20 to 45 degrees, most preferably about 30 degrees) away from the front surface so that it will not point at a bioreactor vessel on the vessel receptacle.

In a method aspect of the invention, a bioreactor vessel of the invention, system of the invention or array of the invention is to grow a culture of biological cells. In particular embodiments, when an array is used, the contents of the vessels of a master bioreactor and an auxiliary bioreactor are mixed by controlling the pressure differential between the vessels.

In "concentric tube" aspect of the invention, there is a disposable stir tank bioreactor vessel such that inside said vessel there is a rotatable shaft, said shaft comprising a plurality (two or more) concentric tubes such that there is a space between each tube and its closest neighboring tube, such that said space is accessible by bioreactor fluid from below (preferably the top of the space is not blocked thereby permitting continuous upward flow of fluid within the space). The size of the space as measured in a horizontal radial direction form the center vertical axis of the shaft is in the range 1 mm to 10 mm (preferably, 1 mm to 3 mm). In particular embodiments, the internal and external surface of a tube is coated partly or entirely with a material permitting cell attachment and growth (preferably adapted for animal or human cells).

The concentric tube invention applies to bioreactor vessels whether or not they are disposable and even if their working volume exceeds 100 ml.

In a "vertical column" aspect of the invention, a disposable stir tank bioreactor vessel comprises internal vertical columns, said columns either solid with an external surface or tubular with both internal and external surfaces. In particular embodiments, inside said vessel there is a vertical rotatable shaft, said shaft comprising a horizontal platform surrounding said shaft, such that the internal vertical columns are either supported by (preferably) or suspended from said platform. Alternatively there is a horizontal platform surrounding said shaft, said platform not attached to said shaft but attached to the internal wall of the vessel such that the internal vertical columns are either supported by (preferably) or suspended from said platform. In particular embodiments, the vessel comprises a head plate, such that the internal vertical columns are suspended from said head plate. In particular embodiments, the internal and external surface of a vertical column is coated in part or in full with a material permitting cell attachment and growth (preferably adapted for animal or human cells).

The vertical column invention applies to bioreactor vessels whether or not they are disposable and even if their working volume exceeds 100 ml.

A "3-dimensional structure" invention is a bioreactor vessel, such that inside said vessel there is a rotatable shaft, said vessel further comprising one or more platforms (for example, discs) centered around and connected to said shaft, said vessel further comprising a three-dimensional structure on said platform, said structure coated at least in part with a material permitting cell attachment and growth (preferably adapted for animal or human cells).

Preferably the 3-dimensional structure has a center of gravity that is located along the central axis of the shaft. Preferably, the 3-dimensional form is symmetrical around the central axis of the shaft, according to an arrangement that permits the axis of the shaft to rotate around a vertical axis without the form asserting forces that try to tip the shaft away from its vertical disposition. Preferably, the 3-dimensional form in combination with the disc has sufficient symmetry around the shaft so that the combination remains balanced as the shaft rotates. In particular embodiment, one or more surfaces of the form is coated in part or in full with a material permitting cell attachment and growth (preferably adapted for animal or human cells).

The 3-dimensional structure invention applies to bioreactor vessels whether or not they are disposable and even if their working volume exceeds 100 ml.

In a "microcarrier screen" aspect of the invention, the bioreactor vessel, comprises, inside said vessel, is a rotatable shaft and further comprises a screen enclosing a space (or volume of fluid) surrounding the shaft so as to not permit microcarriers that are in that space or volume from escaping that space or volume.

The microcarrier screen invention applies to bioreactor vessels whether or not they are disposable and even if their working volume exceeds 100 ml.

Additional inventions are method inventions directed at creating sterile bioreactor systems and vessels: A method of preparing a sterile bioreactor vessel or bioreactor system said method comprising separately sterilizing two components of said bioreactor vessel or system and then combining them in a sterile room under sterile conditions. In particular embodiments, one of said components is a probe or sensor. In some example, the other component is the vessel or system absent said probe or system.

In particular embodiments of the method, one component is sterilized by radiation ( ) such as gamma-radiation). In some embodiments, one component is a probe or sensor sterilized by ethylene oxide. In some embodiments, one component is a probe or sensor that comprises an enzyme.

In particular embodiments of the disposable stir tank bioreactor vessel, other than the stirrer shaft and impeller there are no probes, sensors or other inserts protruding into the interior of the vessel.

In particular embodiments of a disposable stir tank bioreactor system, other than the stirrer shaft and impeller there are no probes, sensors or other inserts protruding into the interior of the vessel.

The preferred embodiment of bioreactor systems (1) and vessels (10) of this invention is shown for example in FIGS. 1A-1B, 2A-2E, 4A-4C 6A-6D and 7A-7G. Typically, the dimensions of the shown system is about 4.0" wide, 8.0 inches long (or 4.25 inches wide, 8.5 inches long) and the height for about half that foot print may vary between 10 and 13 inches, depending on the position of the tilt-able display (2) at the top surface (20). The height for the remaining half, "lower surface" (21) is about 2.5 inches. However, it is understood that for the same configuration, different dimensions are possible, extending or shrinking the internal space of the system depending on the dimensions of the components needed to be housed within. For clarity, the term bioreactor vessel refers to the culture vessel and the term bioreactor system refers to the entire system including bioreactor controller (3), accessories as well as the bioreactor. The hemispherical base (13) of bioreactor vessel (10) is seated into a counterpart hemispherical receptacle (22) in lower surface (21). (The base optionally is not totally hemispherical but may have the shape of part of a hemisphere.) The receptacle is a constitutive part of a heating block, which provides the heating or cooling to the bioreactor to control temperature by convective transmission of energy across the contacting surfaces. A resistive temperature detector (RTD) placed in a port within the rim (14) of the bioreactor provides for temperature monitoring and is part of the bioreactor temperature feedback control.

The external radius of the hemispherical bioreactor bottom (13) and the internal radius of the heating block (50) are made as close as possible, almost identical, so as to permit close fit between their respective surfaces. A heating blanket (51) provides energy to heat the block and a Peltier device or a fan may be used for cooling. Heating or cooling the block provides the temperature control needed by the bioreactor. The heating block is made from a heat conductive material such as aluminum.

Bioreactor

The bioreactor envisioned in this application contains features that allows it to be used as a versatile small stirred tank cell culture system, without inserts in the culture other than agitators (stirrers). All sensors, i.e., dissolved oxygen (DO), pH, temperature, carbon dioxide ($CO_2$) etc., are "outside or in the wall" type. The "full" capacity of the stirred tank may be used to culture cells without obstructions.

The bioreactor system of the present invention includes the bioreactor vessel, a motor (43) attached to the head plate of the vessel, a stirring shaft attached to the motor, a bioreactor controller (3) which can support the vessel and enclose a controller board (75, a/k/a microprocessor) and support a pump manifold, The head plate, stirrer shaft and vessel are disposable. The motor may be connected by electrical lines (34) to the bioreactor controller.

The bioreactor vessel (10) can be molded as one single piece, or as two pieces: 1) an upper cylindrical portion, and 2) a bottom portion (13) which is a hemispherical base, that portion also comprising a rim (14) and a drainage tube (17). The two portions can be attached to each other by glue, welding, or by any other manner of joining them together in a leak-proof manner. A head plate (11) can then be attached to complete the bioreactor.

Accordingly, the vessel (10) comprises three segments: A bioreactor base (13) a cylindrical vessel segment (6) and a head plate (11). The first two can be combined, for example, by molding them as a single piece or by combining them by using an adhesive or other mechanical method. The bioreactor base is preferably hemispherical. The head plate can be reversibly attached and secured to the top of the wall of the cylindrical vessel. Its removal allows full access into the vessel. The reversible attachment can be accomplished, for example, by a screw-type design. An "O" ring or gasket (100), anchored in the head plate can be used to seal the head plate to the rim of the wall of vessel.

An extended rim (14) (a rim with an outwardly hanging lip) along the top of the bottom portion of bioreactor vessel consists of two portions; the external rim (15) and the internal rim (16); the two portions are separated by an air gap (19), where the gap is compartmentalized by placing ribs (32) between the external and internal rim portions along the perimeter of the rim; the gap between the rims may vary in each compartment and the length of each compartment may vary.

The "double rim" provides a layer of insulation for greater temperature control. It provides a convenient means for attaching sensors located in the air gap to the wall of the vessel; i.e., the inner wall (16) provides a transparent window to the vessel and the outer rim wall (15) may be used to anchor and position the sensor in the rim. In the case of the temperature sensor, it may be inserted into a well in the inner rim wall (16), followed by insulation of the gap between the rims and securing the leads from the probe to the outer rim wall (15). Additionally, for full penetrations through the rim and vessel inner wall, such as for insertion of ports and conduits across the rim into the vessel, the double wall provides a convenient means to secure and seal such inserts in the rim body; this may be simply achieved by adding adhesive to the gap between the rims or by using a clip to secure the penetration.

Other uses for the rim (14) include: One, It may serve as a platform to position and retain the bioreactor once the bioreactor base is placed in the heating block (50). Two, an enclosed compartment can be formed between the walls of the rims by adding a covering (69) at the base of the gap between the rims. Such a compartment is useful, for example, to store a liquid such as an electrolyte for a pH reference electrode (62) and for forming a junction (63) with the content of the vessel.

A bottom drainage tube (17) in the bioreactor bottom allows for full drainage of the vessel. A large opening may be provided in the bottom drain for high flow requirements to and from the bioreactor. A conduit (18) from the bottom drainage tube (17) may be directed from within the bioreactor system to exit (40) so as to become accessible outside of the system. It is envisioned that agitation drive shaft (9) may be extended where a lower portion of the shaft extends into the drain port bellow; such a configuration may be used to stabilize the drive shaft, keep it centered, and to sparge into the drain port itself to prevent material from the culture from entering and lodging in the port.

One can imagine a combination of bioreactors in which a controller bioreactor (a/k/a master bioreactor) is connected via its drainage tube to the drainage tubes of another bioreactor, an auxiliary (a/k/a peripheral) bioreactor. The content in both bioreactors are rapidly mixed; where the culture of the auxiliary bioreactor effects the culture in the master bioreactor. Any resulting change in process parameters in the master bioreactor elicits the controls necessary to return the process parameters to set values. The controller bioreactor may thus control the culture conditions of a larger auxiliary system. If necessary, the controller bioreactor system controls may control the auxiliary system in part or fully by controlling, for example, the addition of gases to the auxiliary vessel but use the sensors in the controller bioreactor to monitor conditions in the auxiliary vessel; similarly this may be applied to temperature control. The auxiliary bioreactor may be a bag or stirred tank and may be provided equipped with basic accessories required by the larger system.

Figure 5:
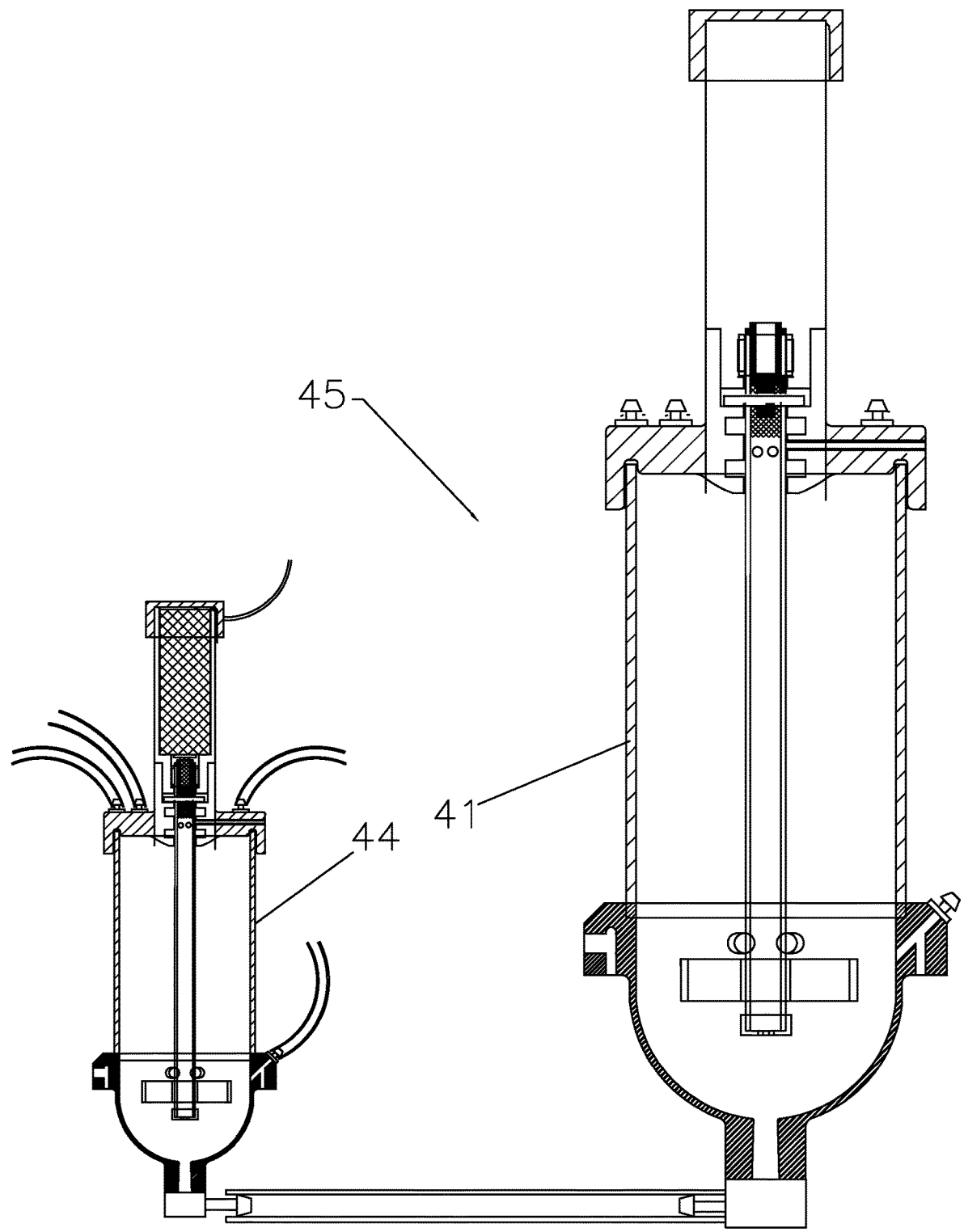
FIG. 5 Partial sectional view of an array of two connected bioreactor vessels of the invention: a controller system vessel and a large auxiliary system vessel.
Figure 6A:
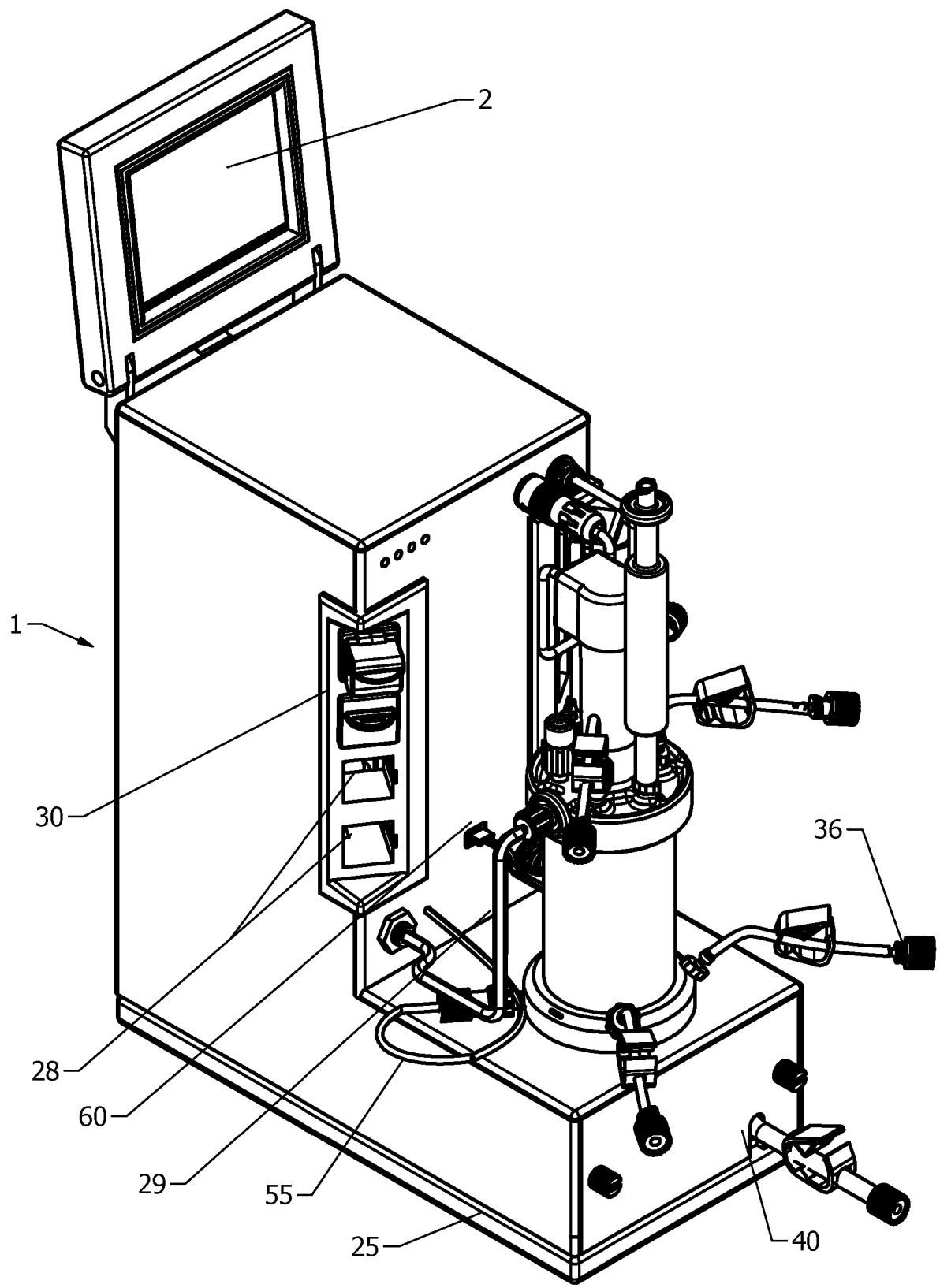
FIG. 6A Isometric view showing the front, left side and top of a bioreactor system of the invention.
Figure 6B:
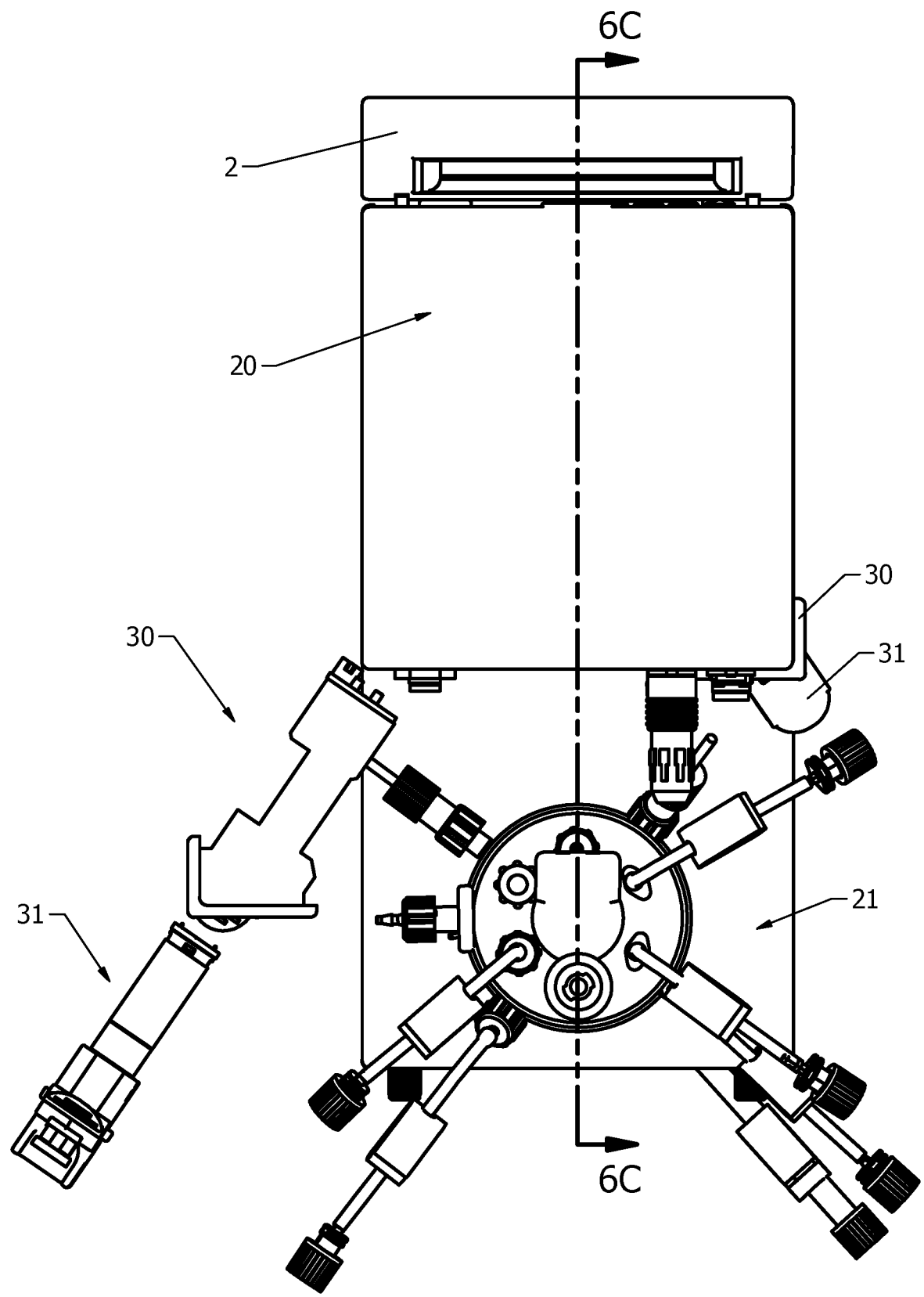
Figure 6C:
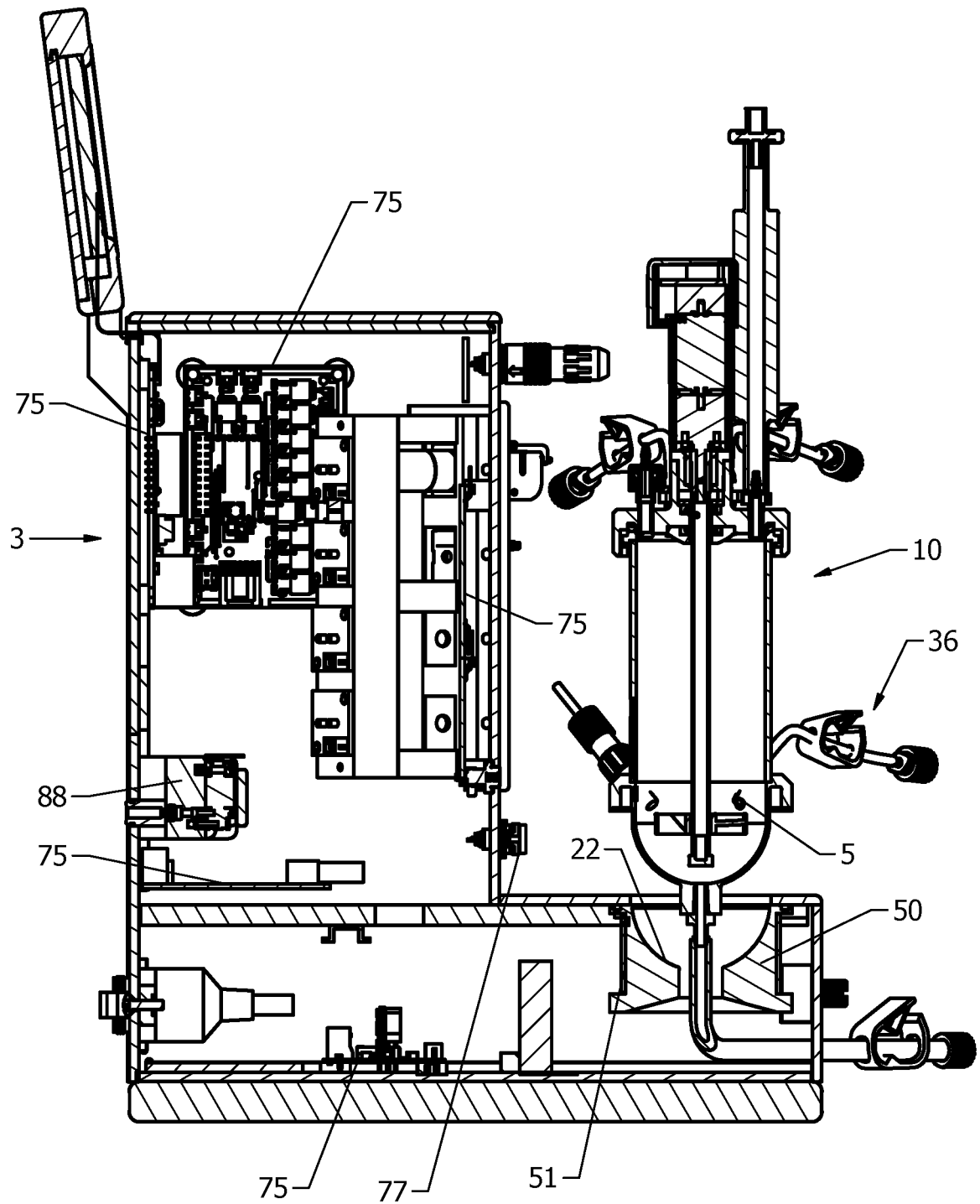
FIG. 6C Cross-sectional side view of the bioreactor system in FIG. 6B taken from the direction of line 6C in FIG. 6B (most visible electrical, gas and liquid lines have been omitted).
Figure 6D:
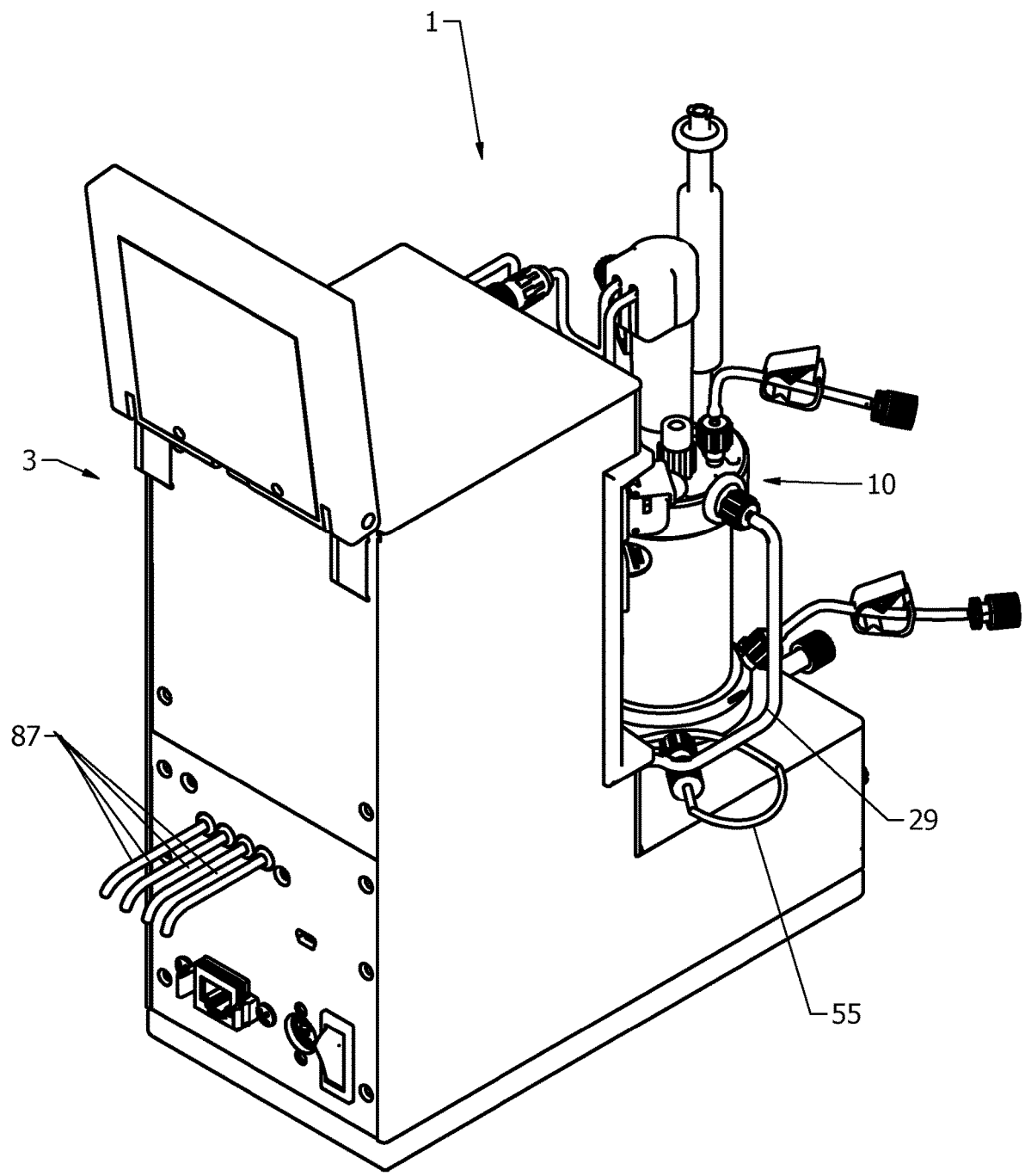
FIG. 6D Isometric view showing the rear, left side and top of a bioreactor system of the invention.
Figure 10:
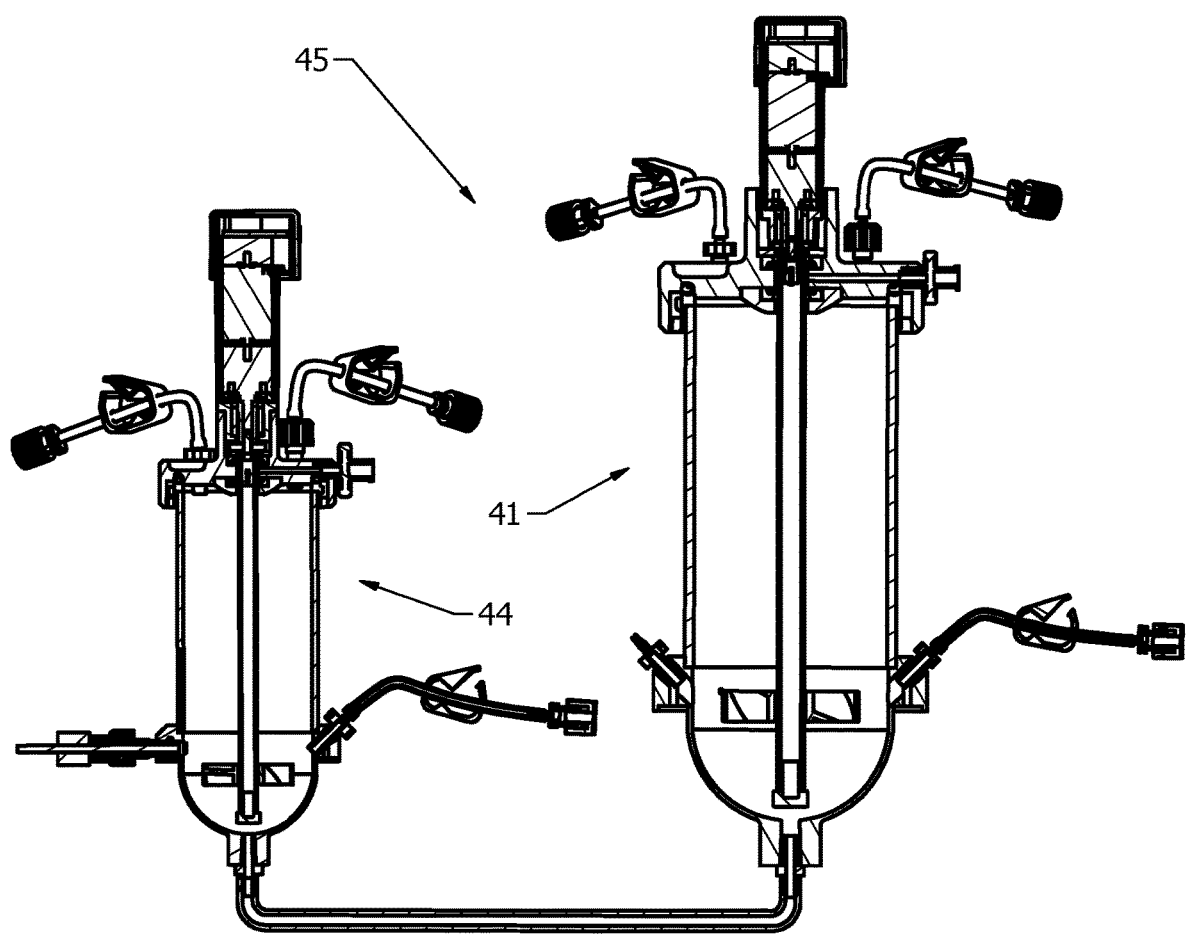
FIG. 10 Partial sectional view of an array of two connected bioreactor vessels of the invention.

The master bioreactor (44) is shown in FIG. 5 and FIG. 10 to be connected to a drainage tube (17) of another bioreactor, an auxiliary bioreactor (41) via a conduit (18) from the drainage tube to form a bioreactor array (45).

Accordingly, the content in both bioreactors may be rapidly mixed by controlling the pressure differential between the two vessels; that is, the pressure differential may be achieved by adjusting the relative pressure in each vessel with a gas flow controller or a valve assembly or with a reversible pump. The rapid reversible flow between the two vessels causes the content of the auxiliary bioreactor to affect the culture in the controller) bioreactor; which in turn, as indicated, any deviation in the content in the control (master) bioreactor will elicit the controls necessary to return the culture to set values; thereby, also affecting the conditions in the larger auxiliary vessel.

If necessary, the controller bioreactor system may control the auxiliary system in an indirect way. Rather than measuring and controlling the process parameters in the master bioreactor only, the measurement is made in the master bioreactor but the control is executed in the auxiliary vessel; i.e., a drop in dissolved oxygen is detected in the master vessel, but the addition of gases or oxygen is directly to the auxiliary vessel. Similarly, a decrease in pH is detected in the auxiliary vessel but a base is added directly to the auxiliary vessel until the desired pH is restored. Because of the rapid equilibration between the two vessels, any change in the auxiliary vessel is rapidly reflected in the controller vessel allowing the controller to respond to the change. Such control may be applied to temperature control, pH, DO, glucose concentration, amino acids as well as any other nutrient.

The auxiliary bioreactor may be a bag or stirred tank and may be provided equipped with basic accessories required by the larger system. Shuttling the content between the two vessels is one way to equilibrate the two. A continuous recirculation loop between the two vessels is another way.

The head plate (11) of the bioreactor is designed to provide full access to the vessel, by its removal from the top of the bioreactor. A screw or latching mechanism allows unscrewing the head plate (11), exposing the top and allowing full access to the vessel. The access to the bioreactor is facilitated by the small size of the bioreactor and the bioreactor system as a whole.

The small size of the system makes it possible to power the entire system with a reasonably small battery pack (25); such a battery pack may be provided quite thin, "approx. ½" thick within the foot print of the bioreactor system; the battery pack may be mounted at the base of the system, so that the entire system may be moved and relocated without compromising the culture. The entire system may, for example, be relocated to a biological safety hood. A rack of vials or tubes containing the essential nutrients may accompany the system during its relocation. A small gas (oxygen) tank, such as, Part number K870M2 from Cramer Decker Medical, Santa Ana, CA may also accompany the system. The ability to relocate the system into a biological safety hood permits exposure of the culture by removal of the head plate. Preferably the head plate only partially removed and attached to a retaining device; this allows both access to the culture while maintaining agitation and sparging of oxygen to the culture during handling. Placement in a biological safety hood also permits making or breaking connections to the culture in a sterile manner.

Sparging or addition of gases may also be accomplished through the drainage port (17) and conduit 18) or bottom side port (5) and conduit (36).

The head plate (11) of the bioreactor also offers means (a head plate conduit (26)) for directing gas flow from its source to the impeller shaft (9) so the gases can be directed to the bottom of the shaft or at any point along the impeller shaft. With the top of the shaft blocked, the gas flow is directed into the bottom of the shaft where it emanates into the culture through a porous frit or other openings. With an impeller (8) that also contains a "draft tube" (7) at its periphery, the discharge of gases at the base and center, such draft tube (7), can facilitate both the agitation process and the gas transport into the culture suspension; in such a case, gas flow and liquid flow may be selected to be concurrent or countercurrent. (For examples of an impeller See FIGS. 3A-3D.)

Figure 7A:
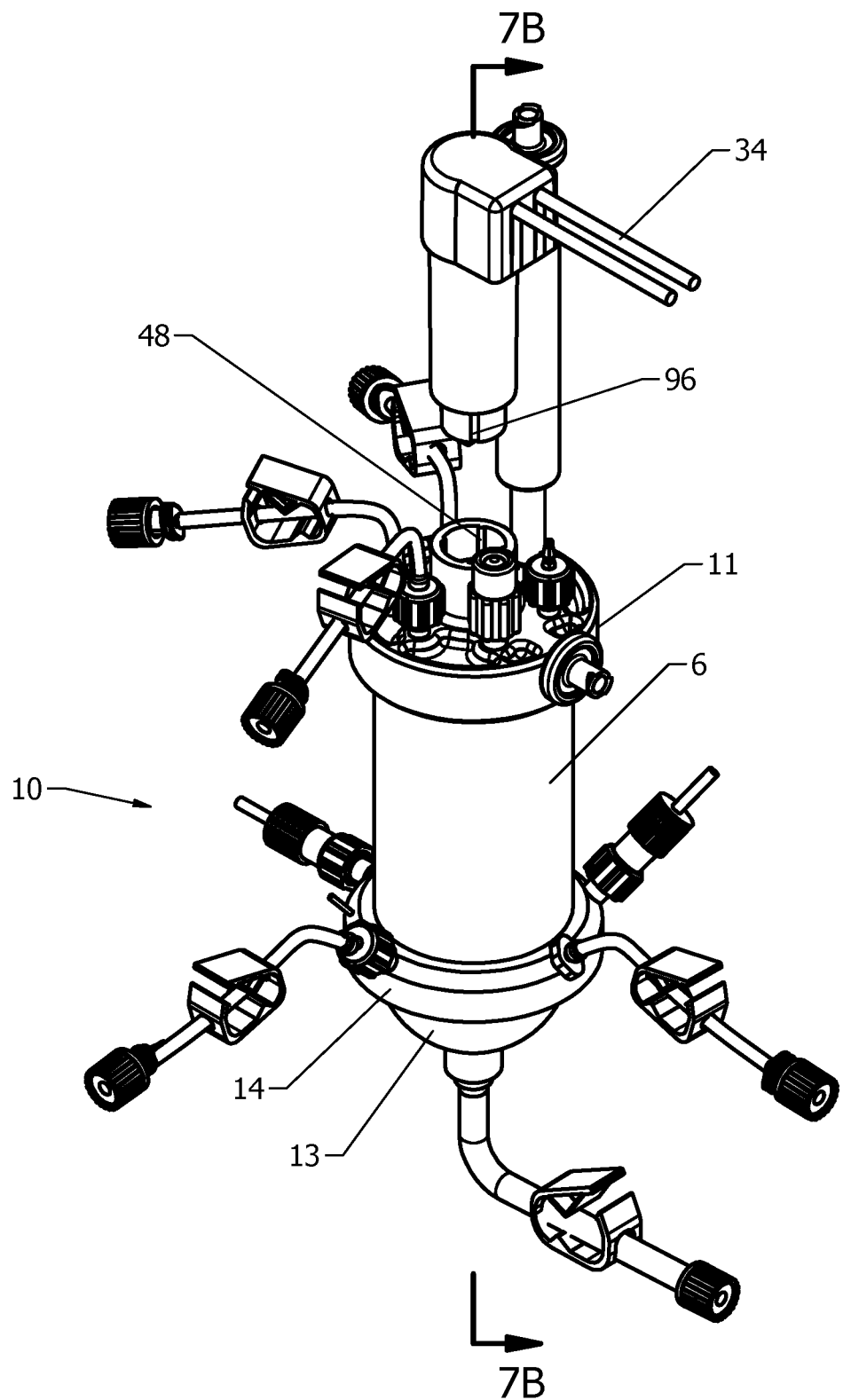
FIG. 7A Perspective view from above of a bioreactor vessel of the invention.
Figure 7B:
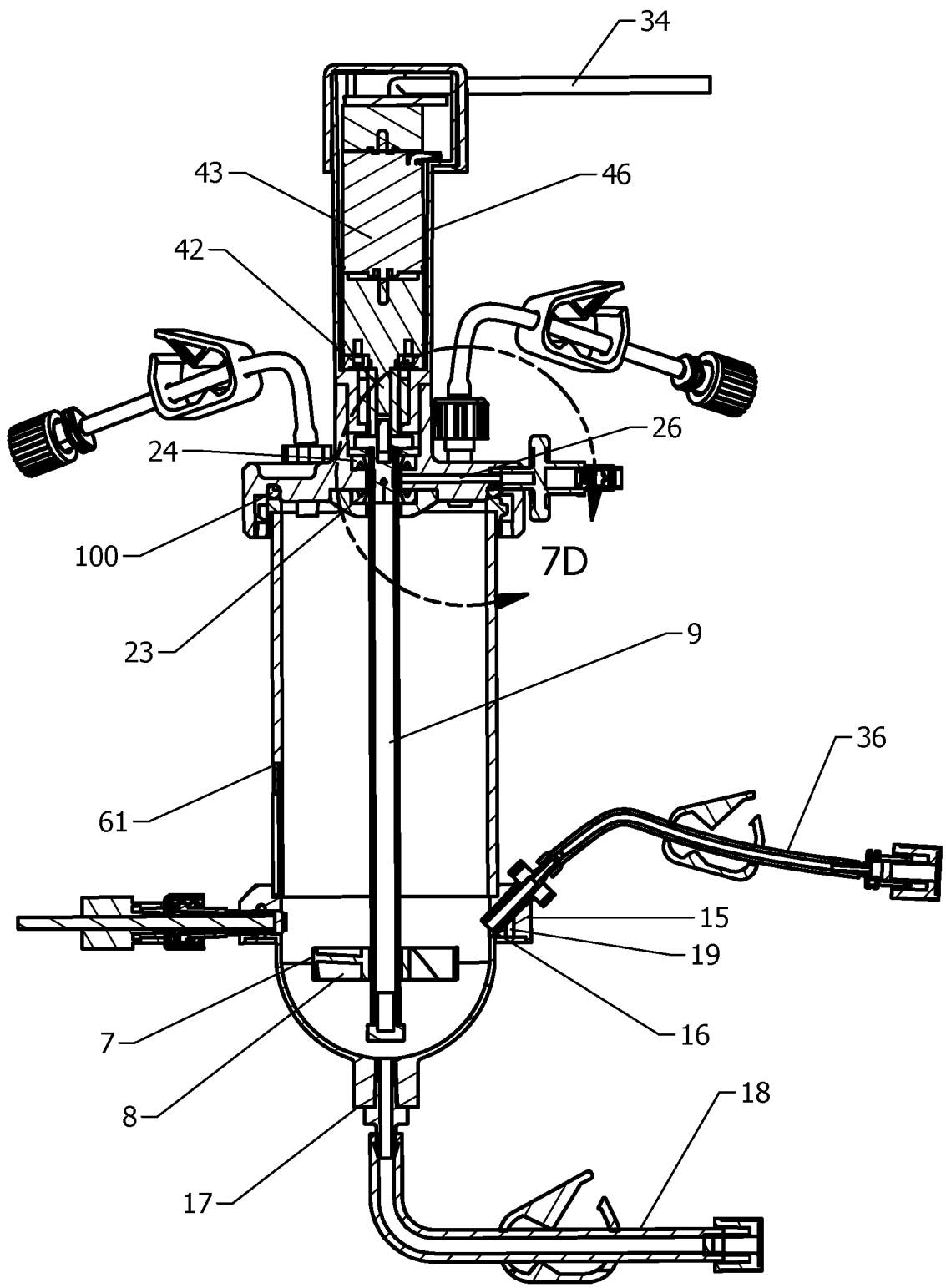
FIG. 7B A cross-sectional view taken along line 78 in FIG. 7A.
Figure 7C:
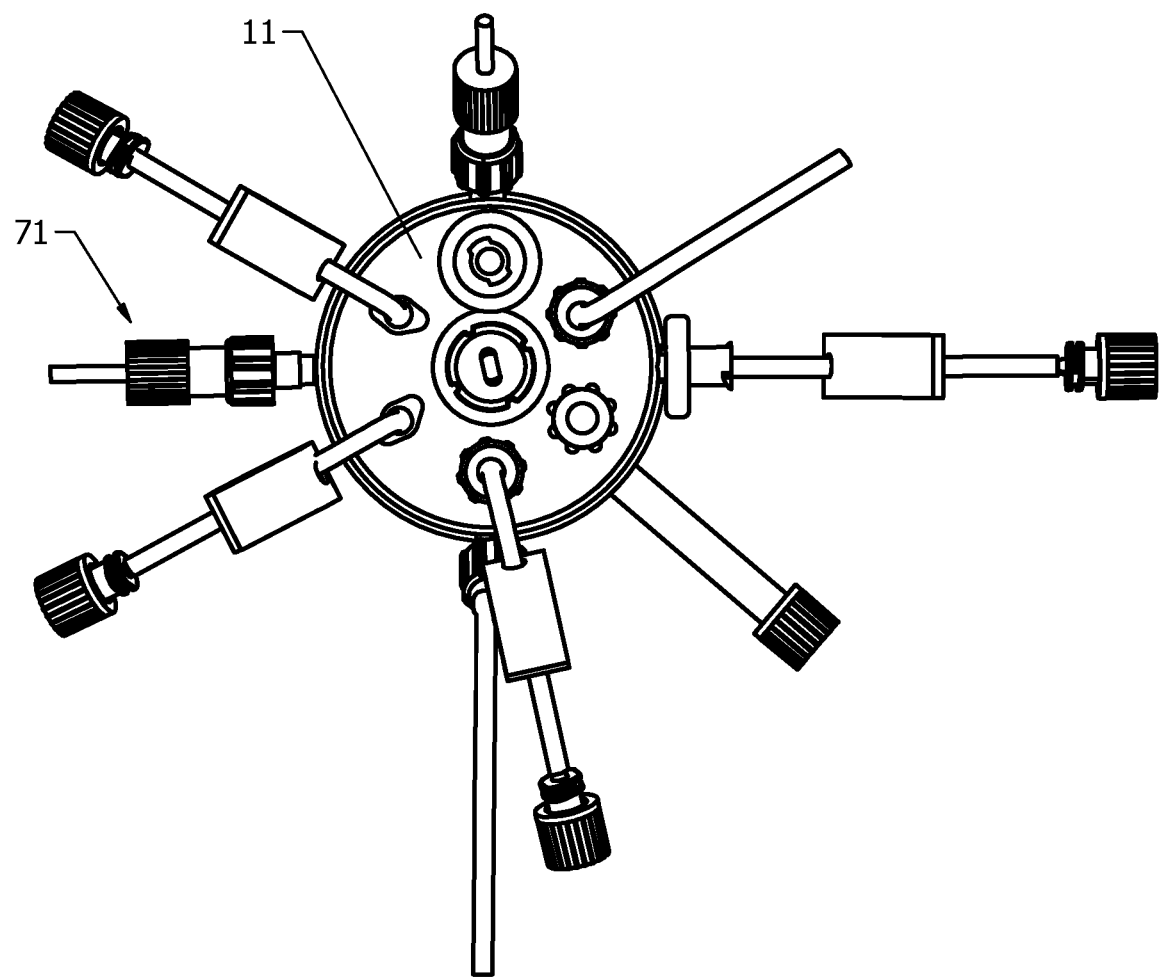
FIG. 7C A top view of a vessel with a head plate.
Figure 7D:
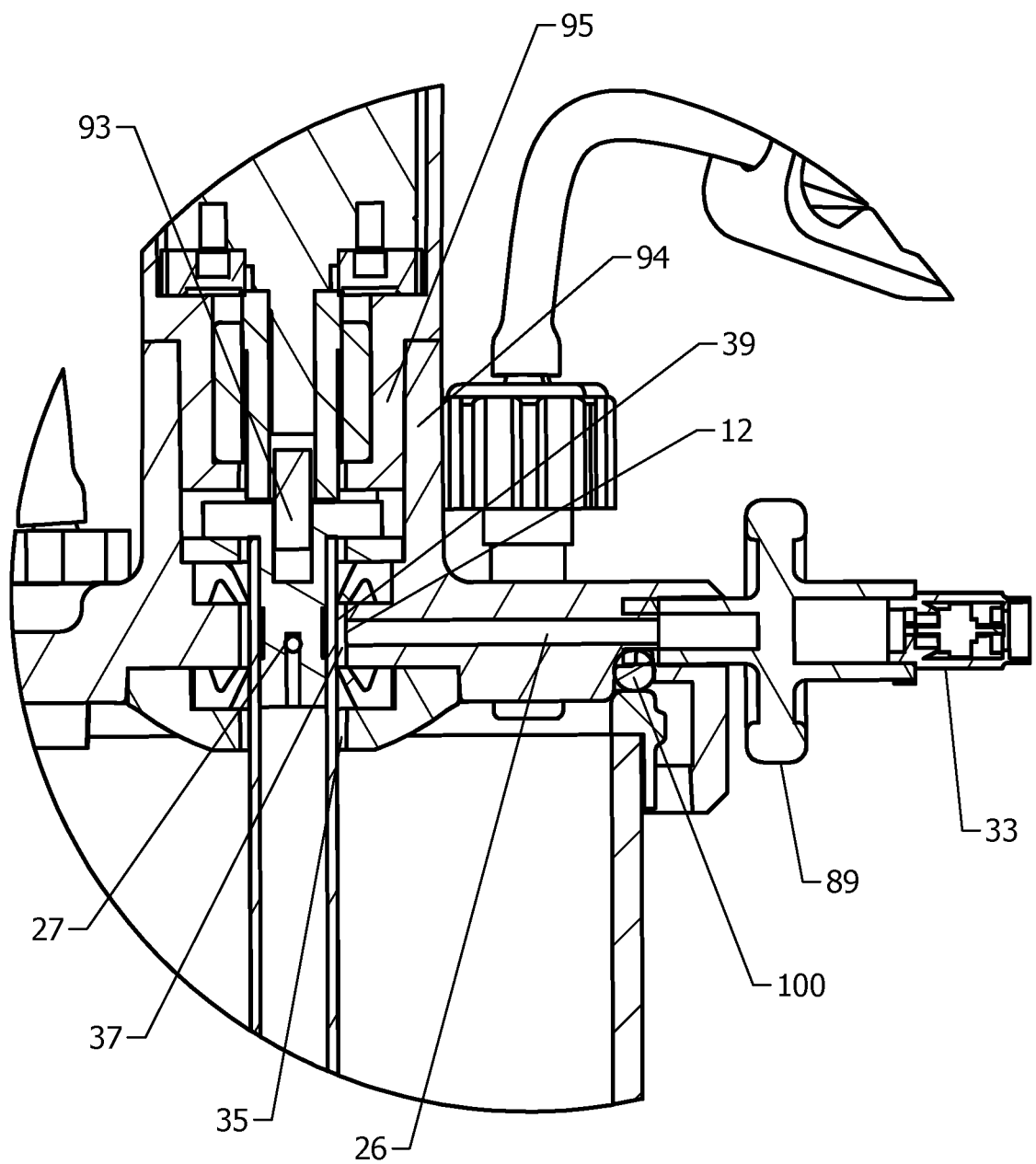
FIG. 7D An enlarged view of the area enclosed by dashed circle 7D in FIG. 7B.
Figure 7E:
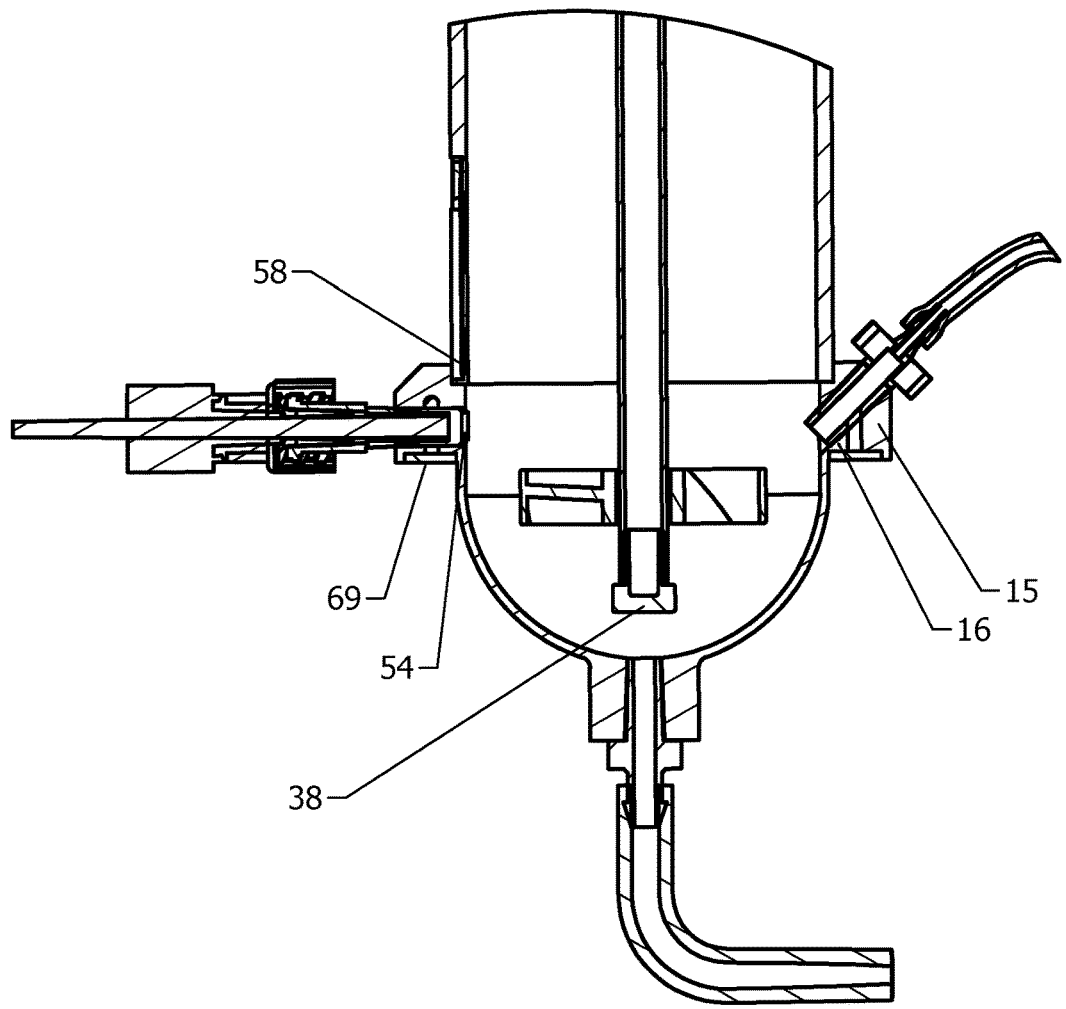
FIG. 7E Cross-sectional view of lower portion of a bioreactor vessel.
Figure 7F:
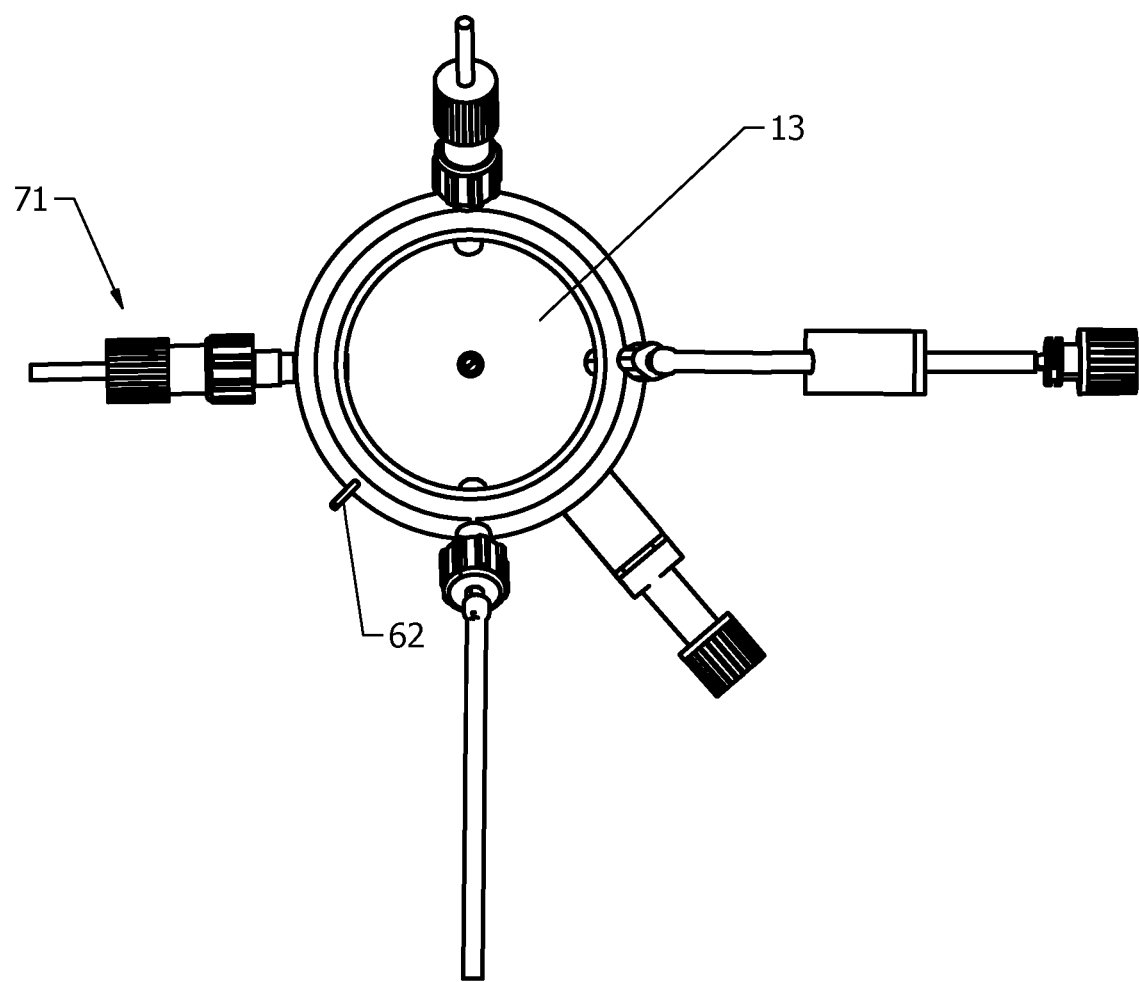
FIG. 7F A top view of a vessel without a head plate.
Figure 7G:
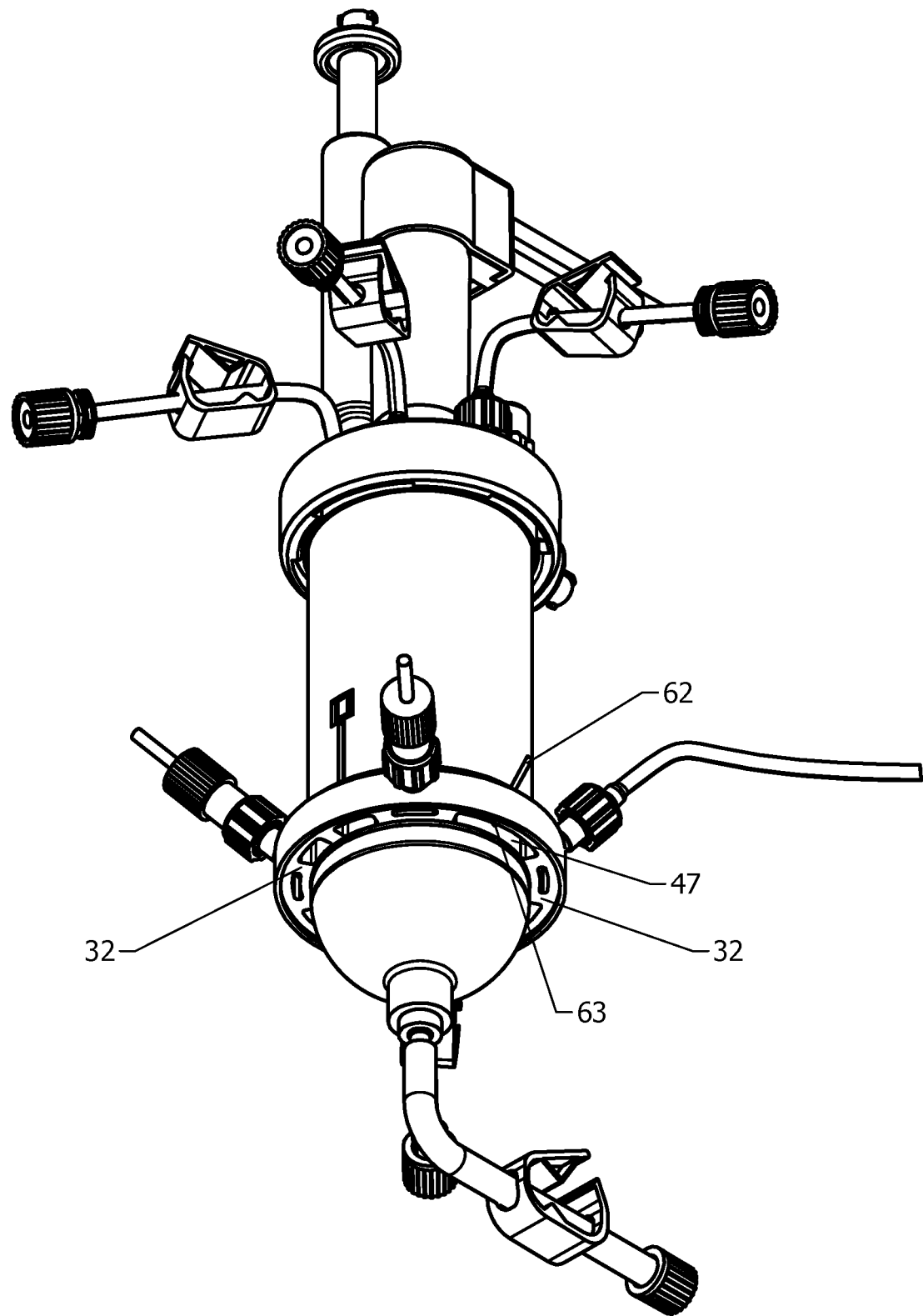
FIG. 7G Perspective view from below of a bioreactor vessel of the invention.

Gas can be directed to conduit (26) from its source via a four-gas manifold outlet (88). Gas enters the four gas manifold (88) via lines (87), passes through the manifold and through a line (not shown) to a gas outlet (77) in front of the controller housing. (The lead line associated in the Figures with the number 3 for the bioreactor controller (3) also points to the controller housing (3).) Gas can, for example, be directed through a conduit (29) to the head plate (11) or the bioreactor vessel. An opening (27) in the impeller shaft wall allows gas to flow from the outside to the inside of the tubular shaft. Either a filter (89), preferably a 0.2u filter (2 micron filter), and/or a check valve (33) may be placed anywhere along the gas supply path from gas source through conduit (26), but preferably at the entrance to conduit (26). The exit opening (12) of conduit (26) results in discharge of gas into an air tight cavity (37). The outer wall of the cavity correspond to the inner walls (39) of a center channel (35) positioned along the center axis of the head plate. The inner wall of the cavity is formed by the outer surface of the impeller shaft tube (9). The upper and lower walls of the cavity, above and below shaft opening (27) and exit opening (12), are formed by opposing mechanical slip seals (23, 24). Details of the air tight cavity are shown in FIG. 7D.

The cavity is air tight as long as an opening (27) in the shaft is not aligned with conduit (26) so as to allow gas to flow into the shaft). When such an alignment does exists any pressurized gas flow into cavity (37), is directed into opening (27), into the shaft tube to be discharged, through a sparge frit (38), such as a porous frit, at the bottom of the shaft or at any point along the impeller shaft.

Additionally, the head plate serves as a coupling interface between an agitation motor drive shaft (42) and the culture agitation system (e.g., agitation drive shaft (9) and an impeller (8)). As noted, two sealing rings (24) and (23) above and below the orifice (12) confine the gases emanating from the head plate (gas) conduit (26) in the head plate. The gases are thus directed to enter the impeller shaft (9) through holes (27) in the tubular impeller shaft; it assures a positive pressure between the sealing rings (24) and (23); the positive pressure in turn serves as a barrier against the infiltration of contaminants into the sterile environment between the sealing rings.

The head plate also serves as a coupling interface between agitation motor is readily achieved by common techniques, such as a lovejoy type coupler (93); furthermore, the motor and motor housing (46) are attached and aligned with the head plate by a lock and key type mechanism, such that when the key (95) on the motor housing coupling segment is inserted into a corresponding receptacle (94) or "lock" in the head plate, the two parts are aligned when combined. Grooves (96) on the outer surface of the motor key and ribs (48) on the inner surface of the head plate receptacle "lock" (94) segment, are also engaged. As a result, when the lock and key are combined, the motor housing and head plate are secured, aligned and prevented from rotating relative to each other. Once the agitation motor is fixed in its housing (46), any torque generated by the motor is transferred directly to the agitation shaft.

Assorted penetrations in the head plate provide means for exit of exhaust gases and ports for addition of liquids as is common in stirred tank systems.

More specifically, assorted probes and ports in the head plate and the base of the bioreactor, and also a drain port at the bottom of the bioreactor base, provide means for accessing and manipulating the culture during an active culture operation. For example, ports in the head plate provide means for exhaust of gasses with or without a condenser in the exhaust line. Head plate ports provide means for addition of nutrients to the culture; one may, optionally, use such ports for inoculation, sampling, placement of sensors, etc. Ports in the base of the bioreactor provide direct access to the culture. Selecting probes, sensors and ports, and coupling devices that largely adhere to luer-type fittings standards allows the user of the invention to select from a very large pool of couplings and connectors as well as other accessories.

Sensors

As indicated, one of the primary objectives of the invention is to provide an integrated culture system with a single use "stirred tank" culture vessel. Another preferred objective is to minimize or eliminate all inserts from the vessel. As indicated, such insets can interfere with the performance of the culture by affecting the flow dynamics in the culture, by serving as surface to which cells adhere, by hampering the reversible access through the top of the vessel, by interference of the probes with the process of removing the head plate; additionally most sensors tend to be expensive and their application in single use bioreactors is somewhat uneconomical one must also consider that many sensors are unstable, may require frequent calibrations and require a time consuming and risky sterilization process. For the stated reasons, it is preferable not to insert various sensors into the culture through the head plate.

An added benefit of clearing the vessel of inserts is the possibility that the resulting cleared space may be used for other functions. What is envisioned in this invention is a stirred tank culture vessel with maximum availability of work volume, that is readily disposable and that can be provided presterilized.

The following are examples of sensor placements:

Dissolved-oxygen sensor placement: In one configuration, an opening (65) is formed in the bottom rim (14), across both rim walls (15 and 16). Preferably the opening dimensions is compatible with reception of a male luer fitting, FIG. 8B. A male luer fitting (52) with a capped end, where a disk (54) with embedded oxygen sensitive dye is attached to the outer, or external end of the luer cap (49). (such oxygen sensitive sensor disks, of various diameters, are commercially available from PreSens, Ocean optics, and other companies). The cap end of the male luer is inserted through the opening in rim (14) and glued therein in a leak proof manner. The sensor is thereby, exposed inside of the bioreactor. A female luer lock at the other end of the said male luer fitting (52) provides a receptacle that may receive a second male luer lock fitting (53) which male luer lock fitting at its other end contains a compression fitting (64). A fiber optic cable (55) is inserted into that second, compression, fitting (64), through the compression end of the male luer lock and through the male luer lock other end. The fiber optic cable (55) may be secured within the second fitting (53) by tightening it on to the cable with the compression end; while at the other end, through the male luer end, the fiber optic cable is extended for a distance such that by inserting the second male luer fitting (53) into the first female luer end, of fitting (52), the fiber optic cable is also inserted, but further into fitting (52) by a determined distance.

Figure 8A:
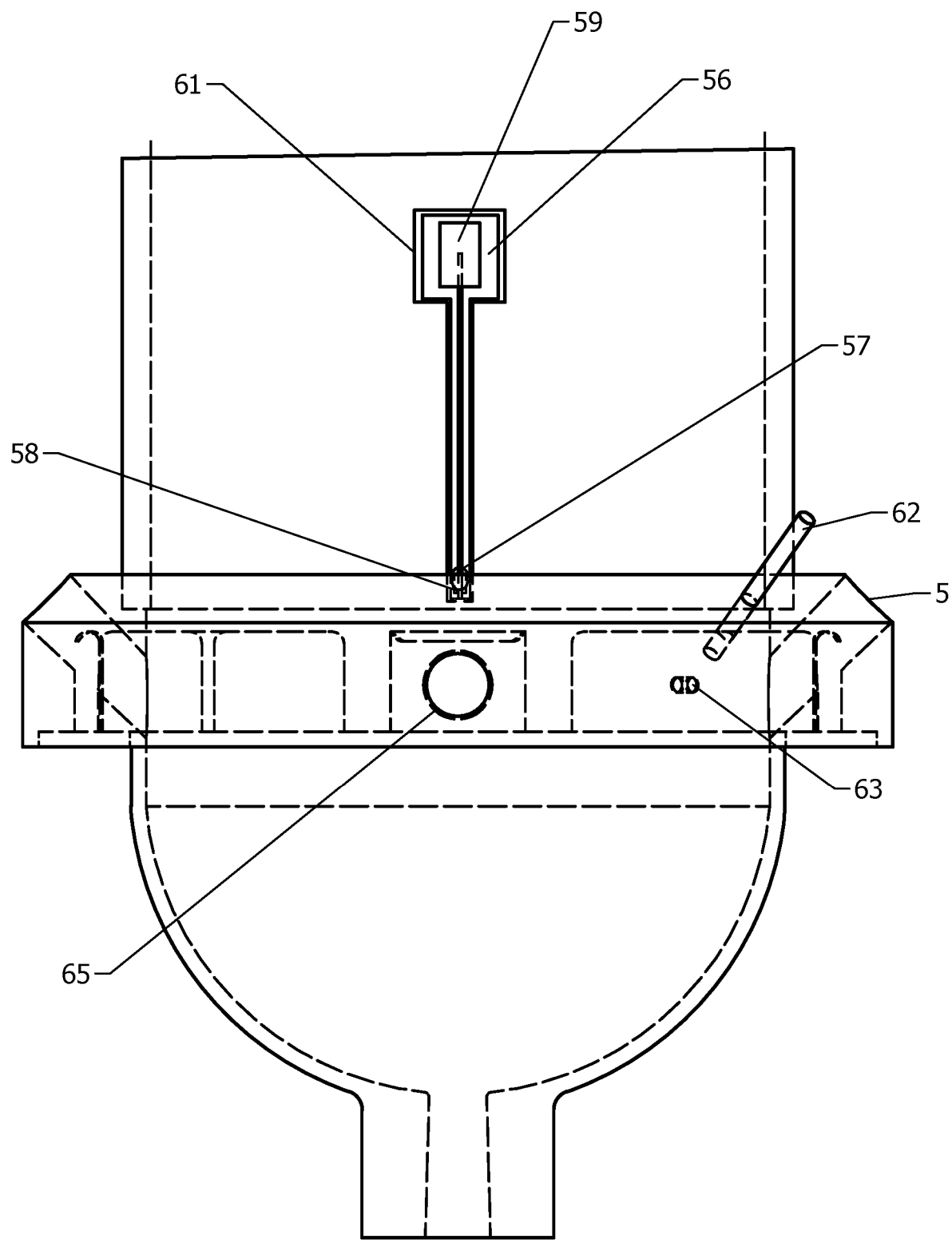
FIG. 8A Schematic view of a portion of a bioreactor vessel showing an ISFET pH sensor in the wall of the bioreactor and also a reference electrode in the vessel rim. Compare FIG. 7G to see wall groove for the ISFET sensor.
Figure 8B:
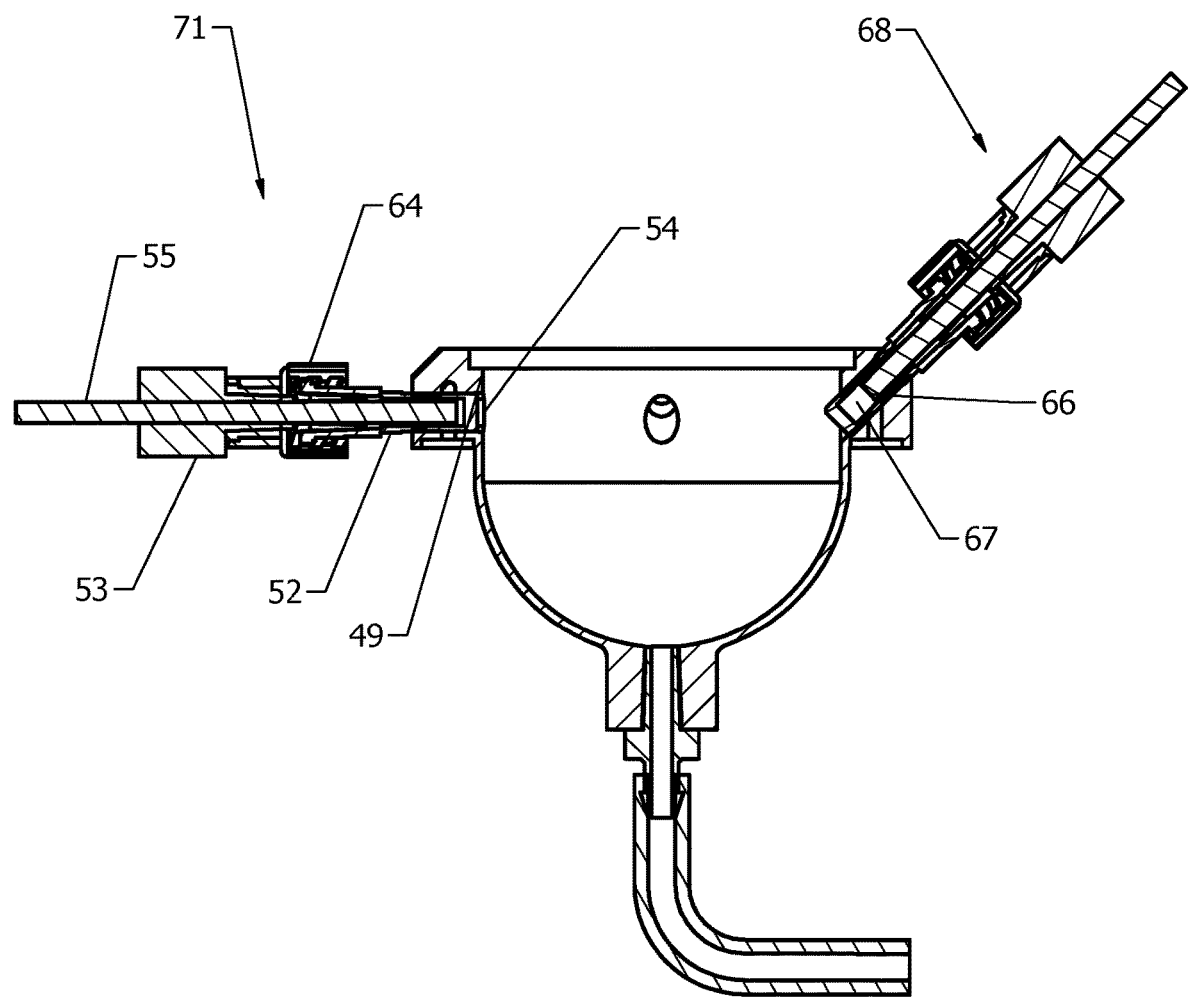
FIG. 8B Cross-sectional side view of the lower portion (approximately one-third) of a bioreactor vessel of the invention showing placement of an oxygen sensor and a temperature sensor.
Figure 9A:
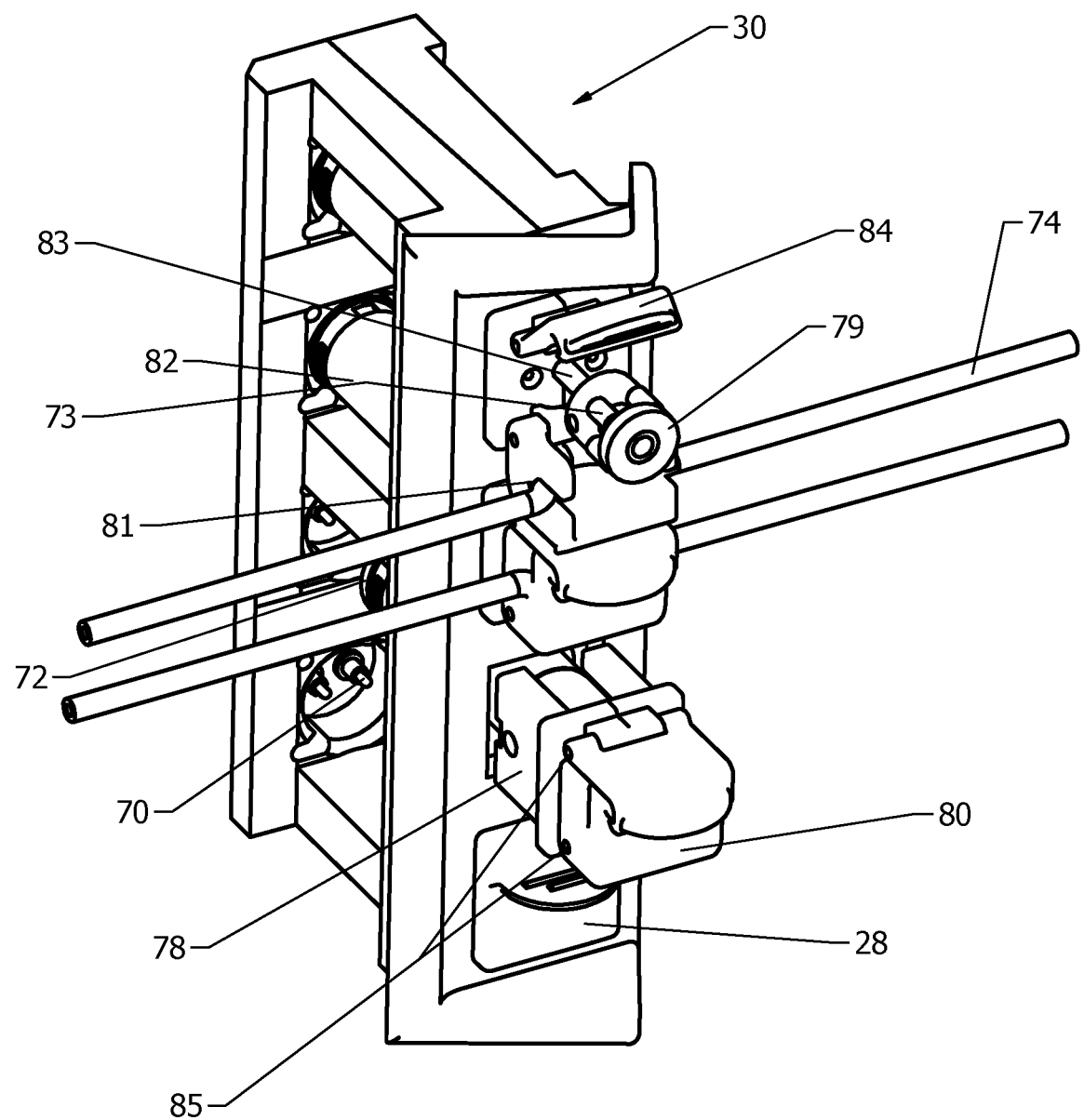
FIG. 9A-9D Perspective views of a pump manifold (30) used in the bioreactor system of the invention, shown from an isometric front view, an isometric rear view, a side view, and an exploded view, respectively (the pump head (79) in FIGS. 9A, 9C and 9D has been displaced forward in those Figures)
Figure 9B:
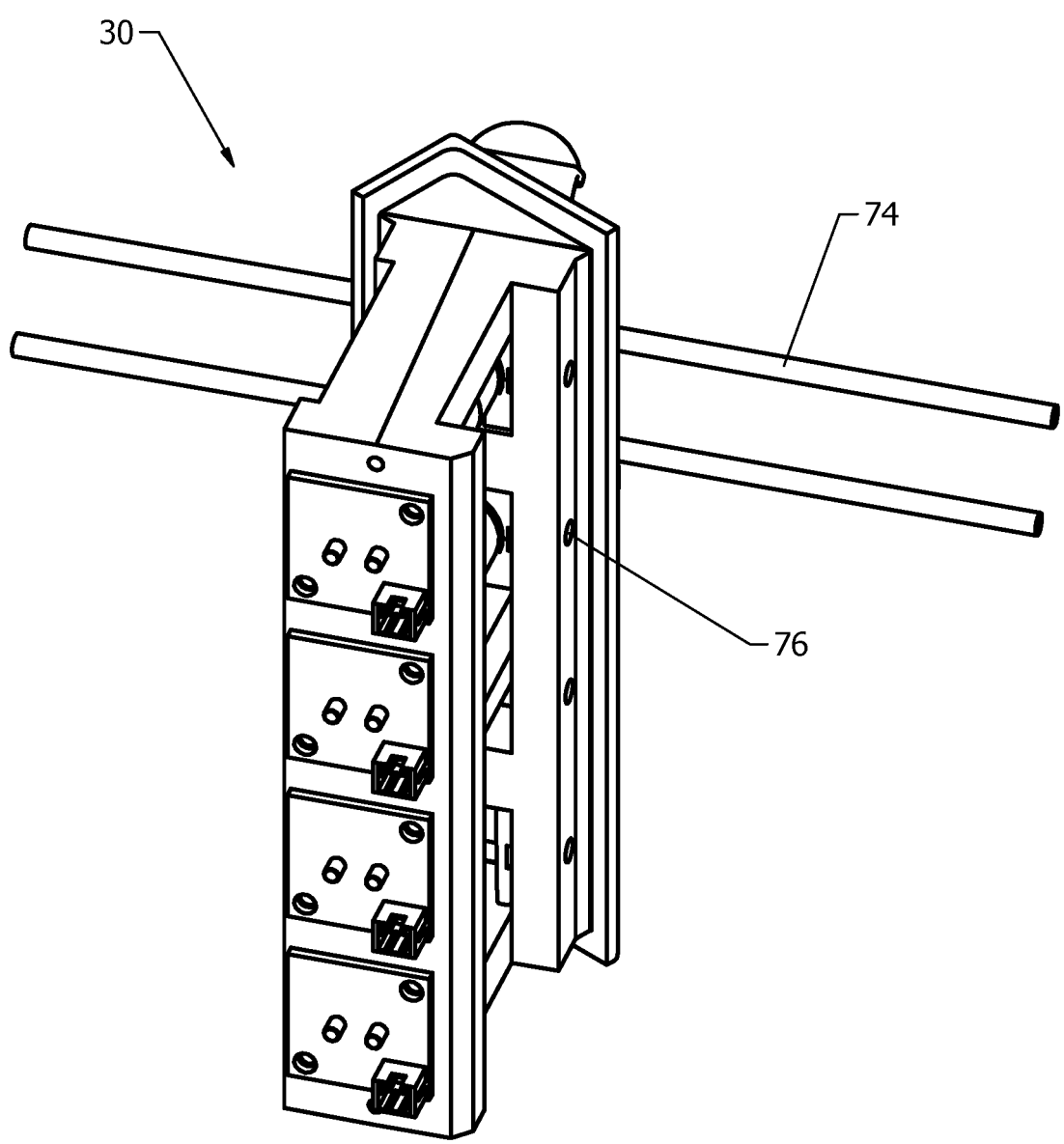
Figure 9C:
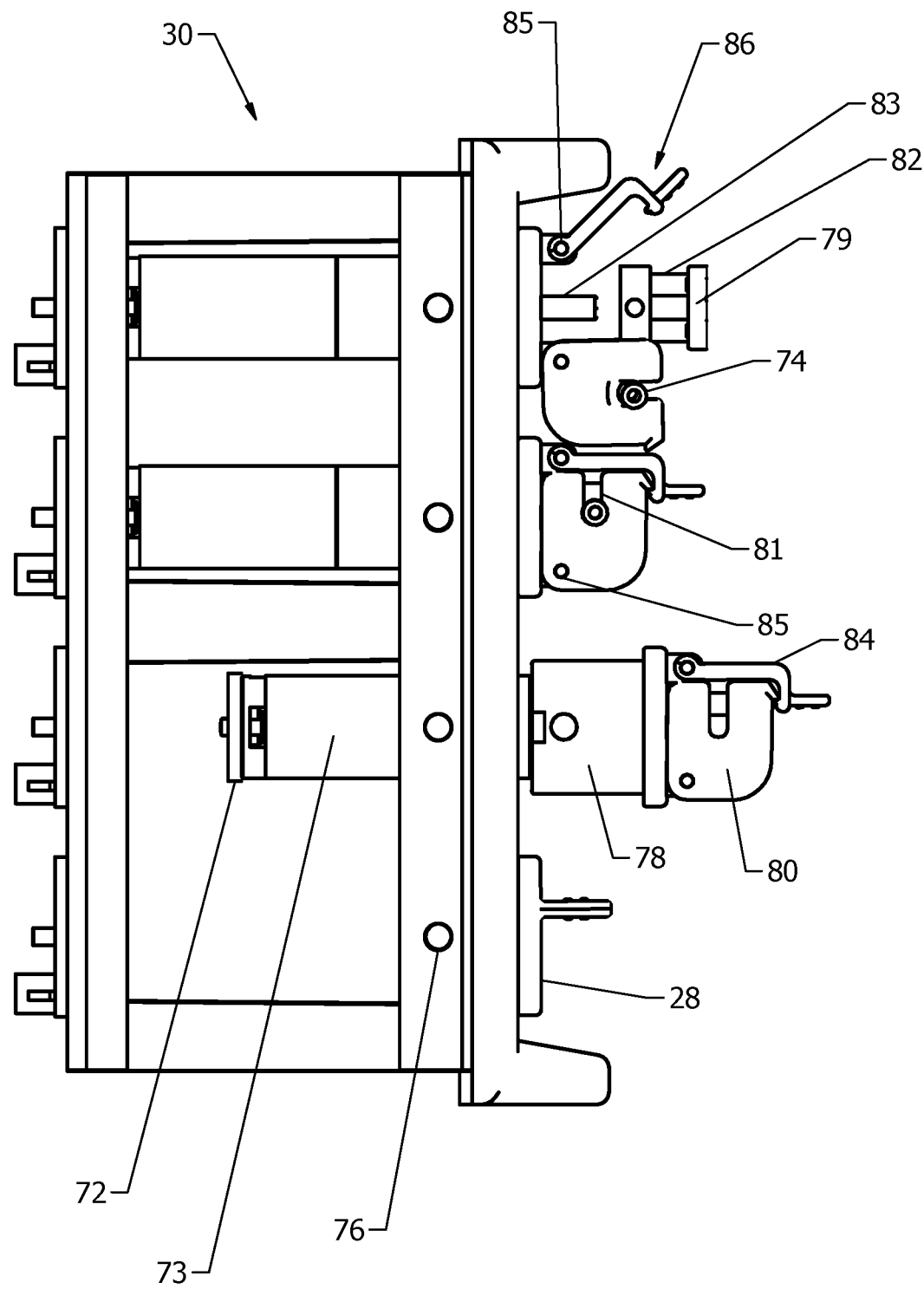
Figure 9D:
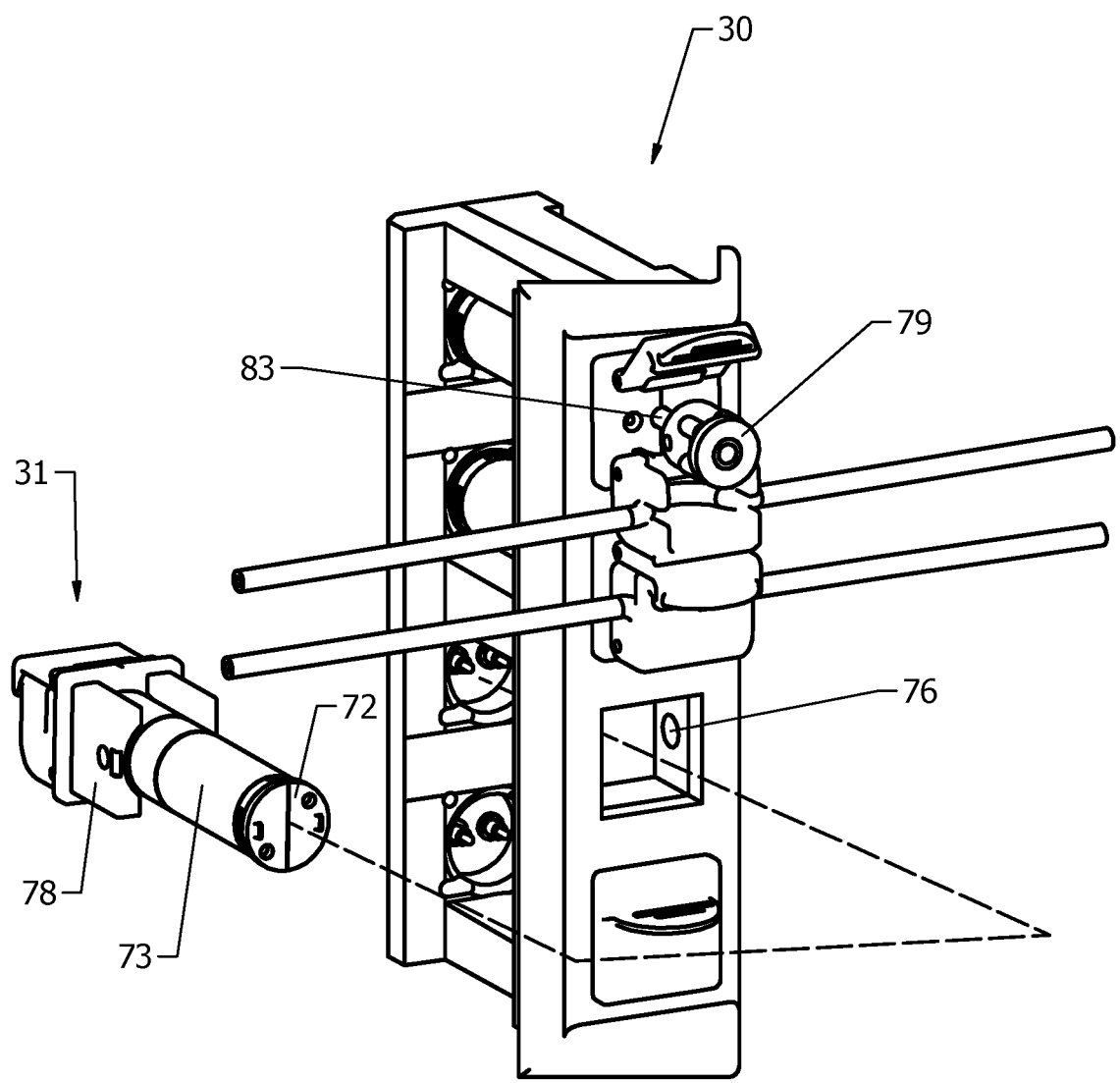

By locking respective luer fittings, the fiber optic is positioned and locked relative to a sensor. This provides a convenient, very repeatable and reversible method for connecting the bioreactor oxygen sensor (71) with the bioreactor controller through a fiber optic cable. The connection for the oxygen cable may be placed horizontally (i.e., perpendicular to the center axis of the vessel) or at an angle, such as 45 degrees from horizontal, or any other angle. An example of the foregoing male/female leur lock—fiber optic cable—oxygen sensor combination is illustrated in FIG. 8B.

Temperature sensor: Similar to the oxygen sensor, the same arrangement of luer fittings is used, to form a thermo-well (67) which positions and secures a resistance temperature detector (RTD) (66) in the bioreactor. The temperature of the thin cap end of the male luer end that faces to the inside of the vessel closely represents the temperature of the vessel contents. Addition of liquid into the thermo-well itself displaces the air within it to facilitate heat transfer. Inserting a thermo-well adapter (68) into the rim (14) at an angle, such as a 45 degree from horizontal facilitate retention of the liquid in the thermo-well. (Illustrated in FIG. 8B)

pH sensor: As in the case of the oxygen sensor, pH may be measured optically by applying a disk with an embedded pH sensitive dye or probe. (FIG. 8A)

The position of the blunted luer inserts, described above, may be varied to facilitate functionality. The angle of the luer fitting insertion relative to horizontal plane of the vessel rim (14) may be varied from zero to 90 degrees, preferably from 15 to 45 degrees.

The pH may also be measured using a galvanic type sensor based on ion-sensitive field-effect transistor (ISFET) technology. Such a probe is placed in the wall of the bioreactor. A slit or a groove (61) in the wall of the vessel (10) with a width and length corresponds to the dimensions of the ISFET (58). An example of such an ISFET device is obtainable from Sentron, Netherlands. A small opening (57) is made through the wall of the vessel. The dimension of the hole corresponds to the ISFET sensing electrode tip size (58), about or less than one $mm^2$. The depth of the hole is minimized to position the sensing electrode as close to the culture as possible, in order to minimize channeling through the hole and to minimize deposition of cells or other constituents which may effect the pH; preferably, a slightly elevated sensing electrode tip (58) is pressed through the hole and so that is flush with the inner surface of the vessel. An adhesive coating deposited within the groove or channel which contains the ISFET and/or, optionally, an adhesive on the ISFET may be used to adhere the ISFET within the groove of the vessel wall. The ISFET, which can be <1 mm wide and formed on a ribbon<0.5 mm thick, can than be fully embedded in the groove with a potting agent or adhesive. (The electrode tip must be protected during the potting process.) It is understood that the sensing ISFET electrode tip (58) must remain unobstructed, conductive and exposed to the inside of the vessel. Other electrical contacts must remain unobstructed to allow electrical conductivity. All adhesives and potting agents, on the other hand, must have low water uptake and remain good insulators. The connection (59) from the ISFET to the controller board (75) may be directly or through a bridge cable (60). The circuit is complete with the reference electrode (62), which as indicated before may be embedded in one of the formed rim chambers (47) The chamber contains electrolyte, a conductive bridge to the culture, an opening for adding or removing electrolyte to the chamber and an electrode which closes the circuit with the controller board (75) inside the bioreactor controller.

Sterilization

The single use stirred tank bioreactor and all its components are sterilizable by gamma radiation, as is common in the industry. However, for various reasons, certain selective components of the bioreactor, should they be required, are not gamma sterilizable, i.e., the parts may be damaged when exposed to radiation, they may cast shadows that interfere with sterilization of other parts may become unstable or they may contain active ingredients that become inactivated when exposed to gamma radiation. The ISFET discussed above is one such component. The invention also envisions use of other sensors, eg, enzyme sensors, that will be mounted on the bioreactor like the ISFET; such enzymatic sensors are also damaged by gamma irradiation. It is nevertheless envisioned that the single use bioreactor will be supplied sterile with such labile components. This is achieved by subjecting the bioreactor with all gamma radiation stable components to sterilization by exposure to radiation. The required components that can not be sterilized by radiation will be sterilized by other means, (by heat, chemically, sterile assembly or other known means), that are not detrimental to those components. The parts, sterilized by different means will than be assembled with the gamma-radiation sterilized bioreactor in a clean room to maintain the sterile integrity of the entire single use bioreactor. The ability to incorporate enzymatic sensors into a single use bioreactor system offers new possibilities in the culturing of cells . . . .

Pumps

The miniature peristaltic pumps used in the current invention are shown in FIG. 9A-9D. The motor is attached to a manifold adapter (78). The pump head (79) with roller (82) is mounted along the center axis of the motor drive shaft (83) that protrudes across the manifold adapter. A pump base (80) containing grooves (81) on the sides and a pump cover (84) enclose the pump head (79). Both pump base and cover are hinged (85) on to the manifold adapter in a manner that allows the two parts to open or close over the pump head. A latch (88) allows that closure to be set and secure. Addition of tubing to the pump is simplified by pivoting the pump base from fully closed to expose the side grooves (81), where the tube is inserted, spanning both grooves. Closing the bump base and cover secures the tube across the pump head rollers. The receptacles (28) in the pump manifold are spaced in a manner that permits the pump base (80) to pivot from fully closed in the vertical orientation to fully horizontal position (about a 90 degree rotation), without interfering with the same activity in the adjacent pumps. To control the flow to and from the bioreactor, the bioreactor system is equipped with a manifold (30) or array with multiple pump banks (28) or receptacles, preferably but not exclusively 8 such banks, which are capable of reversibly receiving or removing such pumps (31) (FIGS. 9A-9D). Spring loaded electric contacts (70) in the rear of the receptacles contact and compress against conductive hemidisks (72) in the back of the motors. The two hemidisks are separated and each connected to a respective motor lead to complete the circuit, to power the pumps. A ball nose spring plunger (76) in the side of each pump receptacle compress against the side of the manifold adapter (78); so when the pump is inserted into the pump receptacle (28), the force of the compressed plunger retains the pump in the receptacle. A specified force is required to overcome the plunger force against the pump holder to dislodge the pump. In the same manner, a pumps may be replaced with other pumps, solenoid powered pinch valve or other devices of appropriate size and power requirements. In this arrangement, the bioreactor system provides the user with the flexibility to configure the system as needed by adding as many pumps, or other devices, as required for managing fluid flow and other hydraulics as needed. Placement of the pumps on the front panel of the controller housing in an angled manner, FIGS. 6A-6C, sideways from the front panel plane allows ready access to the pumps. It simplifies addition removal or manipulation of pump tubing; it also allows greater access to accessories in the front panel of the controller housing.

In summary, to control the flow to and from the bioreactor, the bioreactor system is equipped with a manifold (30) or array with multiple pump banks (28) or receptacles, preferably but not exclusively 8 such banks, which are capable of reversibly receiving or removing pumps (31). Electric contacts in the rear of the receptacles power the pumps. In the same manner, a pump may be replaced with an appropriately sized solenoid powered pinch valve or other devices of appropriate size and power requirements. In this arrangement, the bioreactor system provides the user with the flexibility to configure the system as needed by adding as many pumps as required and controlling the individual flow rates. In addition, the ability to relocate the entire system with flexible ability to add or replace pumps allows the user to manipulate the system in the safe confines of a biological safety hood, to make or break tubing connections to calibrate the pumps off line than return the pumps to the bioreactor system. The control system of the bioreactor system provide the control, calibration and monitoring of all such devices.

In the claims, all terms such as "top", "bottom", and "lower end", that refer to the orientation of an item, do so for the situation where the vessel or bioreactor is oriented in its operating position.

Agitation and Culture Platforms

Essentially any impeller may be used with the current stirred tank bioreactor, depending on application and requirements.

It is envisioned however that elimination of essentially all inserts from the stirred tank vessel interior can result in the space that may be used for other devices that were ether difficult or not possible to implement otherwise. Some of these capabilities become relevant when culturing adherent cells, particularly stem cells and important for culturing tissue in two dimensions or in three dimensions. The following are some examples. In these Examples, however, the limitations on bioreactor vessel size or bioreactor system size referred to above do not apply. The Examples represent inventions that are not only applicable to vessels and systems of the sizes described above, but also larger bioreactor vessels and systems.

Figure 11A:
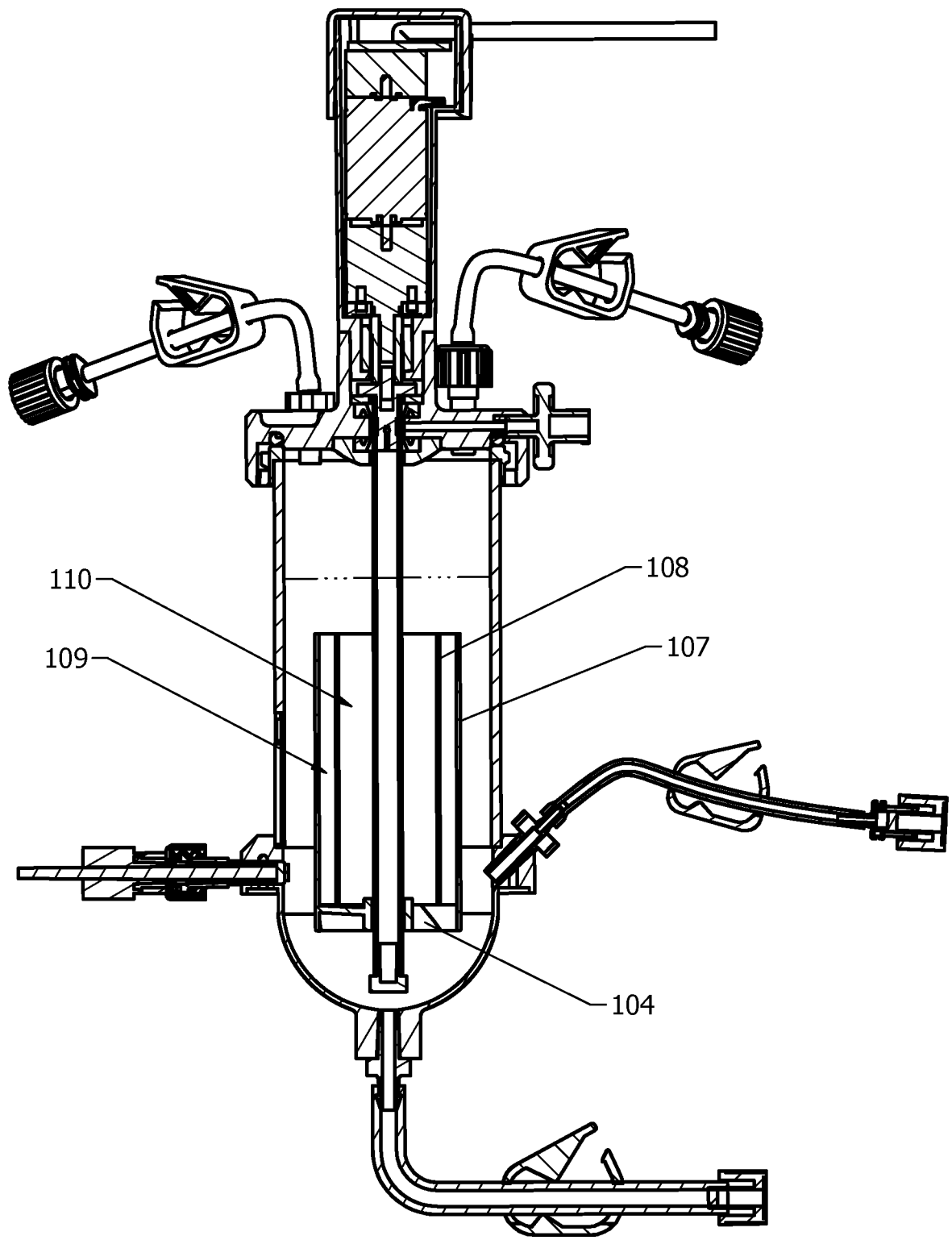
FIG. 11A Partial cross-sectional side view of a vessel with rotating concentric draft tubes.

Example 1. An agitation system combined with a rotating draft tube as shown in FIG. 11A. The flow caused by the impeller can be upward, through the draft tube this flow can be facilitated by bubbles emanating from the sparger in the center of the draft tube. Conversely, the impeller rotation may be in the reverse direction causing a downward flow through the draft tube. In this case, the upward flow of bubbles can be slowed, increasing their residence time in culture for greater oxygen transfer. The liquid flow and gas flow may be adjusted for desired results. The draft tube may serve for culturing suspension cells or adherent cells. Growth of adherent cells is facilitated by coating the walls of the vessel as well as the surfaces of the draft tube with collagenous material or other material that promotes cell attachment and growth. The surfaces of the draft tube may be solid porous or screened materials. The surface area to which cells may attach can be increased by addition of consecutively smaller draft tube rings as shown in FIG. 11A. The external most draft tube is slightly longer, below the impeller, than the inner tubes, which are above the impeller; the external longer draft tube will therefore have the greatest effect on flow direction. All draft tubes must be below liquid level in the vessel. More surface area cam be generated with a higher vessel and more draft tubes. Alternately, the draft tubes may be stationary by their attachment to the vessel interior rather than to the drive shaft. The continuous flow through the draft tubes and their rotation maximizes the homogeneity of the culture. Such an arrangement would be difficult by placing various insets into the vessel.

Figure 11B:
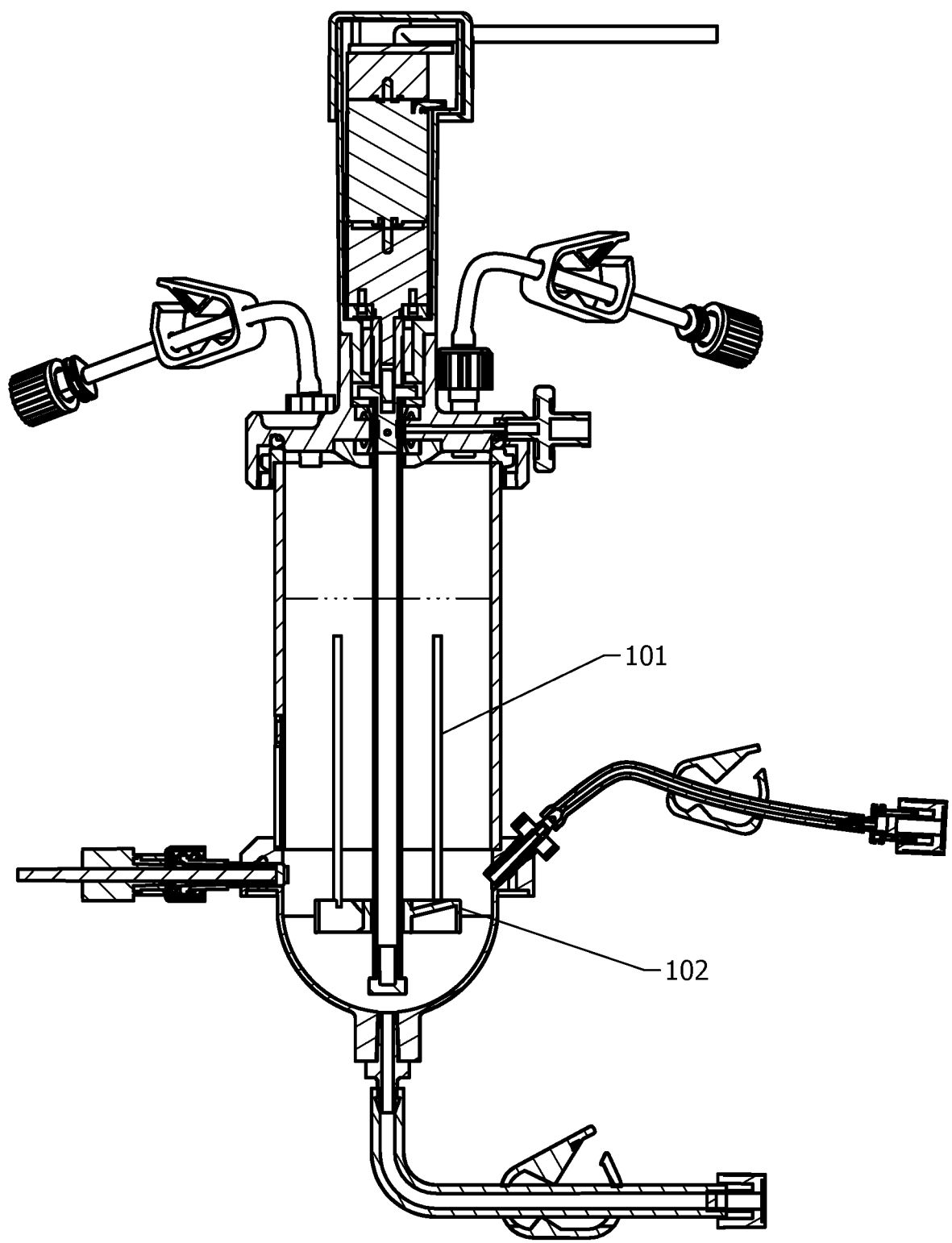
FIG. 11B Partial cross-sectional side view of a vessel with a rotating platform which supports vertical columns.

Example 2. An agitation system with a platform to form tubular tissue is shown in FIG. 11B. A platform (100) attached to the impeller shaft or to the stationary side of the vessel supports vertical columns (101). The columns may be of any desired diameter and length, provided they fit within the confines of the vessel and culture liquid level. The columns may be coated with collagen or any other material that promotes cell attachment and growth. The columns may be solid or tubular and the walls of the columns may be solid or porous. Cells of a particular type may be cultured in the vessel, where the cells adhere to the columns and grow on the columns, forming a tubular layer of cells. A second cell type may than be introduced into the vessel, where the second cell type may attach to and spread on the first cell layer on the column. This may be repeated. Such layering of cells in a tubular form may provide the means to achieve useful tubular tissue.

The tubular tissue may be removed from their support columns either physically, enzymatically or by changing the properties of the incubation medium, ie, by change of pH, change in Ionic concentrations, etc.). Prying off the tubular tissue may be achieved from inside (inside the column) out or from the outside in.

Figure 11C:
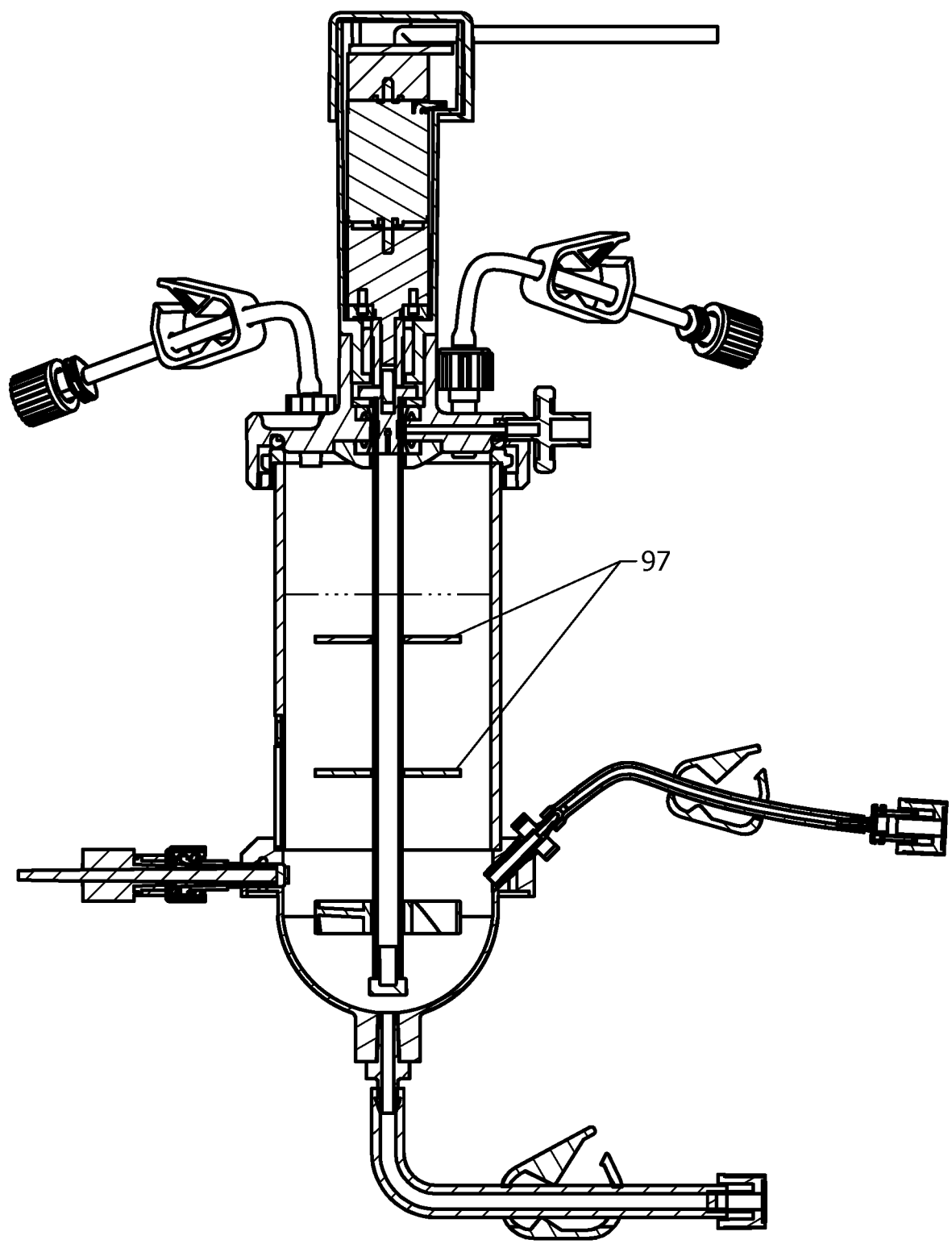
FIG. 11C Partial cross-sectional side view of a vessel with rotating platforms consisting of multiple disks.
Figure 11D:
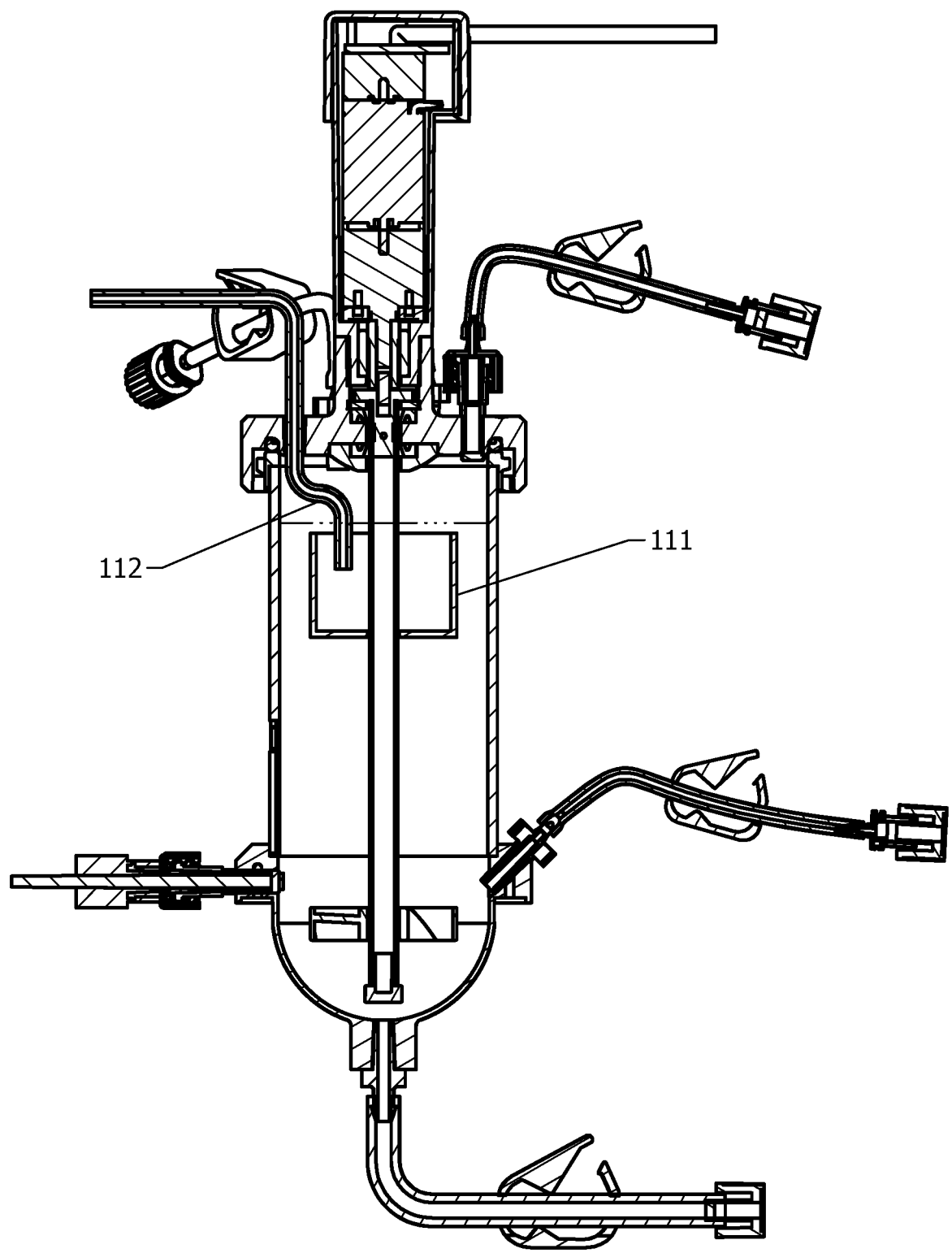
FIG. 11D Partial cross-sectional side view of a vessel with a rotating screened enclosure.
Figure 11E:
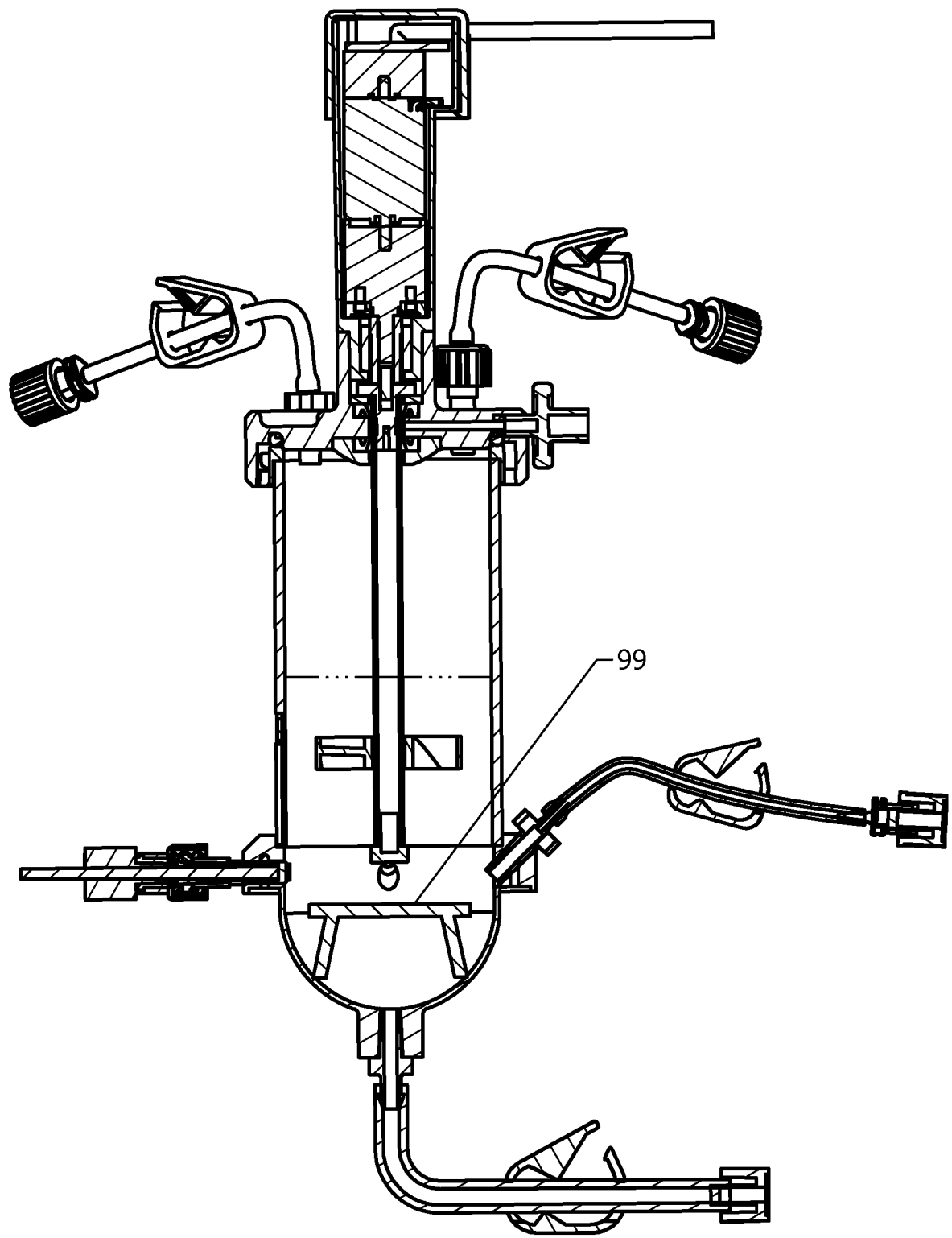
FIG. 11E Partial cross-sectional side view of a vessel with a stationary platform.

Example 3. An agitation system with a platform or platforms. FIG. 11C shows another variation of an agitation platform system consisting of a disk or multiple disks attached to the agitation shaft. A disk may be used as a scaffold that supports a 3-dimensional (3D) form made from collagen or any other material that allows cells to infiltrate the form to generate tissue such as, cartilage, enamel, bone etc. Such a platform may also be placed in a stationary configuration, attached to a stationary part of the vessel, detached from the agitation. (FIG. 11E) The agitation system will continue to mix the culture, circulating the culture over the stationary platform.

Example 4. An agitation system with a screened enclosure as in FIG. 11D. Such system is useful for culturing anchorage dependent cells, grown on microcarriers and for removing microcarrier free medium through the screen. Removing the suspending medium while retaining cells growing on microcarriers is useful for sustaining cultures by perfusion or for washing cells or for medium exchange. This process can be combined with some of the above described examples.

What is claimed:

1. A disposable stir tank bioreactor vessel, said vessel fully assembled, said vessel having a working volume of 100 ml or less said vessel comprising the following:
   a base;
   a cylindrical vessel segment, said segment above the base and combined with the base to form a single piece;
   a head plate, said headplate removable, said head plate comprising openings through which liquids may be added or removed and through which a gas can be delivered into the interior of the vessel, said headplate comprising an opening through which an impeller shaft may be disposed, said head plate comprising a conduit through which a gas can, via a cavity in the headplate, be delivered to the interior of the impeller, said cavity comprising two opposing mechanical slip seals, which seals form the upper and lower surfaces of the cavity, said cavity being air tight when the impeller shaft is rotated at an angle that blocks gas entry into the impeller shaft so that the gas under pressure cannot escape the cavity and ambient air cannot enter the cavity,
   a drainage tube through which fluid can exit the vessel, said drainage tube in the bottom of the vessel,
   an impeller shaft, said shaft vertically disposed in said opening for an impeller shaft, said shaft comprising one end capable of being coupled to an agitation motor and said shaft comprising a frit or other opening for allowing gases to pass from inside the shaft to outside the shaft, a compartmentalized rim, said rim along the top of the bioreactor base, said rim surrounding the vessel, said rim comprising an inner rim wall and an outer rim wall, said rim comprising a rim space, the rim space being a space between said inner rim wall and said outer rim wall, said outer rim wall created by a further extension of a bottom vessel wall, said outer rim wall thereby being a lip of a double rim, said rim space comprising compartments separated by ribs or walls, said rim as a result of its lip comprising an internal portion on its inner rim wall and an external portion on its outer rim wall, which portions are separated by an air gap, said air gap compartmentalized, said inner rim wall being one through which the vessel's content may be accessed, said rim being one to which one or more vessel components can be added, said rim surrounding said vessel, each said component selected from the group consisting of a patch sensor, a port for a connector for use in sampling fluid in the vessel or adding fluid to the vessel, and a luer for placement of a patch sensor,
   said vessel made of a material that is compatible with microorganisms and cells such as mammalian cells.

2. A disposable stir tank bioreactor vessel of claim 1, said vessel fully assembled, sterilized and ready to use, said vessel further comprising the following:
   tubing, connected at one end to a head plate port said tubing allowing additions of fluids, nutrients and inoculations,
   a coupler, said coupler attached to the impeller shaft and capable to being attached to an agitation motor,
   a patch sensor attached to the base of the vessel,
   wherein the walls of the base and cylindrical vessel segment are made of plastic,
   wherein said base is hemispherical.

3. A disposable stir tank bioreactor vessel of claim 2 wherein the patch sensor attached to the base of the vessel extends from inside a rim of the vessel to the inside of the wall of the vessel.

4. A disposable stir tank bioreactor vessel of claim 3 wherein the patch sensor is selected from the group consisting of a temperature sensor, a dissolved oxygen sensor, a glucose sensor, a CO2 sensor and a pH sensor.

5. A disposable stir tank bioreactor vessel of claim 2, said vessel comprising a closed compartment in the double rim, wherein said closed compartment comprises one or more properties selected from the group consisting of being capable of containing fluid, being capable of communicating with the vessel content through a conductive bridge that is in the vessel wall and that spans the vessel wall, being capable of communicating with the vessel content through a conductive bridge spanning the vessel wall, and being capable of having a property of its contents communicated to a controller, and comprising a reversibly closable opening that allows addition to and removal of its contents.

6. A disposable stir tank bioreactor vessel of claim 2, wherein the double rim has one or more properties selected from the group consisting of the following:
   (1) it provides a place for attaching sensors, located in an air gap, to the wall of the vessel,
   (2) its inner wall provides a transparent window to the vessel,
   (3) its outer rim wall may be used to anchor and position a sensor in the rim,
   (4) a temperature sensor may be inserted into a well in the inner rim wall,
   (5) there is insulation of the gap between the rims,
   (6) leads from a probe to the outer rim wall can be secured in the wall, and
   (7) for full penetrations through the rim and vessel inner wall, such as for insertion of ports and conduits across the rim into the vessel, the double wall can be a place to secure and seal such inserts in the rim body.

7. A bioreactor system comprising a bioreactor controller plus a disposable bioreactor vessel of claim 1 and wherein the bioreactor controller comprises the following:
   a vessel receptacle upon which a bioreactor vessel can be placed, said vessel receptacle part of or attached to a heating/cooling block,
   one or two pump manifolds, each manifold comprising a plurality of pump banks (a/k/a receptacles) upon which a peristaltic pump is placed, each pump comprising a motor with a rotatable shaft, a pump base, a pump cover and a pump head, said pump base comprising a surface with a groove, said head comprising rollers, said groove and rollers for engaging tubing and driving fluid through the tube by a peristaltic displacement mechanism,
   spring-loaded contacts for engaging the pumps, replacement pumps, solenoid powered pinch valves or hydraulic devices that manage fluid flow,
   wherein each pump manifold is vertically disposed along on a corner of the controller housing, said corner along the edge of a front surface of the controller housing such that said front surface will face a bioreactor vessel placed on the vessel receptacle,
   and wherein placement of the pumps on the front panel of the controller housing is at an angled manner, sideways from the front panel, thereby allowing ready access to the pumps so as to simplify addition, removal or manipulation of pump tubing.

8. A bioreactor system of claim 7, said system with a footprint not exceeding 100 square inches and a height not exceeding 20 inches.

9. A bioreactor system of claim 7, wherein the bioreactor controller comprises a controller board that controls at least one variable selected from the group consisting of pH, dissolved oxygen, agitation, and temperature.

10. A bioreactor system of claim 7 wherein the system further comprises a battery or battery pack that is connected to and provides electrical power to the entire system in a manner that the entire system may be relocated while fully operational.

11. A bioreactor system of claim 10 wherein the fully operational system is relocated to a safety hood.

12. A bioreactor system of claim 7 wherein the system further comprises both a display screen and a central processing unit that connects one or more patch sensors to the display screen and translates the information obtained by the sensor into an image on the screen, said image comprising features selected from the group consisting of words, numbers, and graphs.

13. A bioreactor system of claim 7, wherein said system is connected to one or more other systems of said claim, thereby forming an array in which each vessel is connected via its drainage tube directly to another of said systems in the array, said connection optionally to the drainage tube of the vessel of that other system.

14. A bioreactor system of claim 7 wherein other than the impeller shaft and impeller there are no probes, sensors or other inserts protruding into the interior of the vessel.

15. A disposable stir tank bioreactor vessel of claim 1, wherein the rim comprises a male luer lock fitted with a patch sensor probe and further comprises a female luer lock adapter.

16. A disposable stir tank bioreactor vessel of claim 15, wherein the rim further comprises both a second male luer lock and a compression fitting to which a fiber optic cable can be reversibly fitted.

17. A disposable stir tank bioreactor vessel of claim 1 wherein other than the impeller shaft and impeller there are no probes, sensors or other inserts protruding into the interior of the vessel.

18. A disposable stir tank bioreactor vessel of claim 1, wherein other than connections to external devices, the vessel is complete and ready for immediate use for culturing cells.

19. A disposable stir tank bioreactor vessel of claim 18, wherein the vessel does not contain cells or cell culture medium but comprises all the parts needed for culturing the cells.

* * * * *